(12) United States Patent
Avrahami et al.

(10) Patent No.: US 7,164,942 B2
(45) Date of Patent: *Jan. 16, 2007

(54) HANDHELD APPARATUS AND METHOD FOR TRANSDERMAL DRUG DELIVERY AND ANALYTE EXTRACTION

(75) Inventors: Zohar Avrahami, Rehovot (IL); Ze'ev Sohn, Ginot Shomron (IL)

(73) Assignee: Transpharma Medical Ltd., Yehuda (IL)

( * ) Notice: Subject to any disclaimer, the term of this patent is extended or adjusted under 35 U.S.C. 154(b) by 440 days.

This patent is subject to a terminal disclaimer.

(21) Appl. No.: 10/775,725

(22) Filed: Feb. 9, 2004

(65) Prior Publication Data

US 2004/0230227 A1 Nov. 18, 2004

Related U.S. Application Data

(60) Continuation-in-part of application No. 09/635,892, filed on Aug. 10, 2000, now Pat. No. 6,615,079, which is a division of application No. 09/189,170, filed on Nov. 9, 1998, now Pat. No. 6,148,232.

(51) Int. Cl.
*A61N 1/30* (2006.01)
*A61M 31/00* (2006.01)
*A61B 5/04* (2006.01)

(52) U.S. Cl. .................. 604/20; 604/501; 600/372
(58) Field of Classification Search ............ 604/19–21, 604/501; 607/2, 3, 152; 600/391, 372
See application file for complete search history.

(56) References Cited

U.S. PATENT DOCUMENTS

| | | | |
|---|---|---|---|
| 3,964,482 A | 6/1976 | Gerstel | |
| 4,175,551 A | 11/1979 | D'Haenens et al. | |
| 4,775,361 A | 10/1988 | Jacques et al. | |
| 4,943,290 A | 7/1990 | Rexroth et al. | |
| 5,019,034 A | 5/1991 | Weaver et al. | |
| 5,135,478 A | 8/1992 | Sibalis | |
| 5,165,418 A | 11/1992 | Tankovich | |
| 5,196,709 A | 3/1993 | Berndt et al. | |

(Continued)

FOREIGN PATENT DOCUMENTS

EP 0547 482 5/1998

(Continued)

OTHER PUBLICATIONS

Henry et al., "Micromachined needles for the transdermal delivery of drug", IEEE 11th Annual International Workshop on Micro-Electro-Mechanical Systems, 1998, pp. 494-498.

(Continued)

*Primary Examiner*—Sharon Kennedy
(74) *Attorney, Agent, or Firm*—Abelman, Frayne & Schwab

(57) ABSTRACT

A device is provided for treating skin on the body of a subject. The device includes a plurality of electrodes, which are adapted to be placed in contact with the skin and then moved across the skin while maintaining electrical contact with the skin. The device additionally includes a power source, which is adapted to apply a current between two or more of the plurality of electrodes at the same time as the electrodes are being moved across the skin.

6 Claims, 11 Drawing Sheets

U.S. PATENT DOCUMENTS

| | | |
|---|---|---|
| 5,232,441 A | 8/1993 | Stephen et al. |
| 5,246,867 A | 9/1993 | Lakowicz et al. |
| 5,281,825 A | 1/1994 | Berndt et al. |
| 5,328,452 A | 7/1994 | Sibalis |
| 5,380,272 A | 1/1995 | Gross |
| 5,409,835 A | 4/1995 | Lakowicz et al. |
| 5,421,817 A | 6/1995 | Liss et al. |
| 5,423,803 A | 6/1995 | Tankovich et al. |
| 5,439,440 A | 8/1995 | Hoffman |
| 5,458,140 A | 10/1995 | Eppstein et al. |
| 5,485,530 A | 1/1996 | Lakowicz et al. |
| 5,500,437 A | 3/1996 | Saitoh et al. |
| 5,571,149 A | 11/1996 | Liss et al. |
| 5,582,168 A | 12/1996 | Samuels et al. |
| 5,624,847 A | 4/1997 | Lakowicz et al. |
| 5,628,310 A | 5/1997 | Rao et al. |
| 5,631,169 A | 5/1997 | Lakowicz et al. |
| 5,648,269 A | 7/1997 | Lakowicz et al. |
| 5,660,991 A | 8/1997 | Lakowicz et al. |
| 5,674,267 A | 10/1997 | Mir et al. |
| 5,688,232 A | 11/1997 | Flower |
| 5,697,896 A | 12/1997 | McNichols et al. |
| 5,720,772 A | 2/1998 | Eckhouse |
| 5,722,397 A | 3/1998 | Eppstein |
| 5,759,767 A | 6/1998 | Lakowicz et al. |
| 5,792,049 A | 8/1998 | Eppstein et al. |
| 5,797,966 A | 8/1998 | Bontoux et al. |
| 5,860,421 A | 1/1999 | Epstein et al. |
| 5,871,469 A | 2/1999 | Eggers et al. |
| 5,885,211 A | 3/1999 | Eppstein et al. |
| 5,902,272 A | 5/1999 | Eggers et al. |
| 5,911,223 A | 6/1999 | Weaver et al. |
| 5,924,981 A | 7/1999 | Rothfritz et al. |
| 5,938,657 A | 8/1999 | Assa et al. |
| 5,964,726 A | 10/1999 | Korenstein et al. |
| 5,983,130 A | 11/1999 | Phipps et al. |
| 5,983,131 A | 11/1999 | Weaver et al. |
| 6,002,482 A | 12/1999 | Rothfritz et al. |
| 6,009,344 A | 12/1999 | Flower et al. |
| 6,022,316 A | 2/2000 | Eppstein et al. |
| 6,024,733 A | 2/2000 | Eggers et al. |
| 6,030,399 A | 2/2000 | Ignotz et al. |
| 6,041,253 A | 3/2000 | Kost et al. |
| 6,045,502 A | 4/2000 | Epstein et al. |
| 6,050,988 A | 4/2000 | Zuck |
| 6,055,451 A | 4/2000 | Bambot et al. |
| 6,066,134 A | 5/2000 | Eggers et al. |
| 6,076,012 A | 6/2000 | Swanson et al. |
| 6,083,196 A | 7/2000 | Trautman et al. |
| 6,088,606 A | 7/2000 | Ignotz et al. |
| 6,090,106 A | 7/2000 | Goble et al. |
| 6,104,952 A | 8/2000 | Tu et al. |
| 6,117,109 A | 9/2000 | Eggers et al. |
| 6,142,939 A | 11/2000 | Eppstein et al. |
| 6,142,992 A | 11/2000 | Cheng et al. |
| 6,148,232 A | 11/2000 | Avrahami |
| 6,159,194 A | 12/2000 | Eggers et al. |
| 6,173,202 B1 | 1/2001 | Eppstein et al. |
| 6,183,434 B1 | 2/2001 | Eppstein |
| 6,192,734 B1 | 2/2001 | Rothfritz et al. |
| 6,210,402 B1 | 4/2001 | Olsen |
| 6,228,078 B1 | 5/2001 | Eggers et al. |
| 6,235,020 B1 | 5/2001 | Cheng et al. |
| 6,238,391 B1 | 5/2001 | Olsen et al. |
| 2002/0010414 A1 | 1/2002 | Coston |

FOREIGN PATENT DOCUMENTS

| | | |
|---|---|---|
| WO | WO 93/10854 | 6/1993 |
| WO | WO 94/16765 | 8/1994 |
| WO | WO 94/27671 | 12/1994 |
| WO | WO 97/07734 | 3/1997 |
| WO | WO 01/13989 | 3/2001 |

OTHER PUBLICATIONS

Chizmadzhev, et al., "Electrical properties of skin at moderate voltages", Biophysics Journal, Feb. 1998, 74(2), pp. 843-856.

"Instructions Manual for the Force 2 Electrosurgical Generator", Valleylab/TycoHealthcare Group LP, Boulder, Colorado, 1999.

U.S. Appl. No. 09/859,646 entitled: Electronic card for transdermal drug delivery and analyte extraction, filed May 17, 2001.

U.S. Appl. No. 09/644,093, filed Aug. 23, 2000, entitled: "Tissue Electroperforation for enhanced Drug delivery".

U.S. Appl. No. 60/150,636, filed Aug. 25, 1999, entitled: "Tissue Electroperforation for enhanced Drug delivery and Diagnostic Sampling".

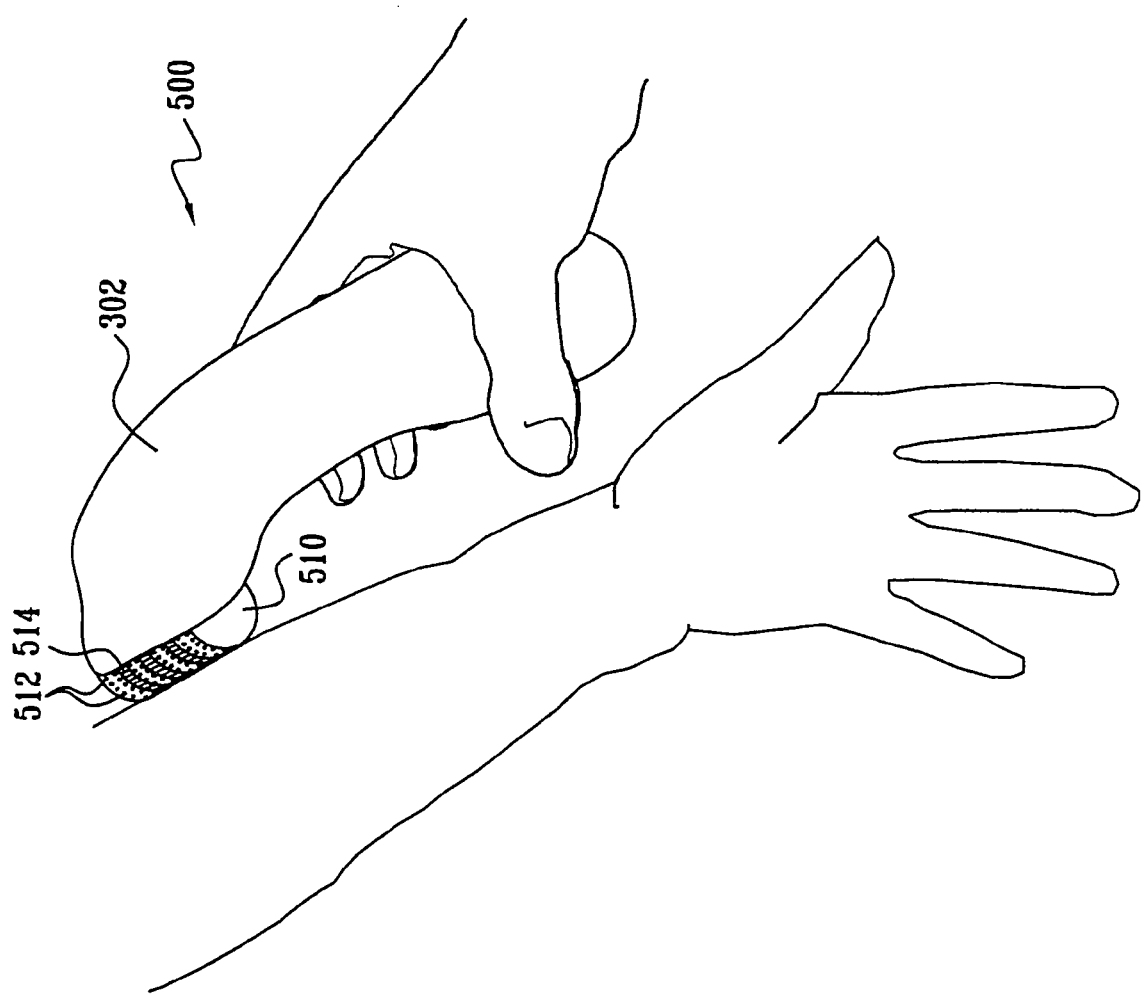

HANDHELD APPARATUS AND METHOD FOR TRANSDERMAL DRUG DELIVERY AND ANALYTE EXTRACTION

CROSS-REFERENCE TO RELATED APPLICATIONS

This application is a continuation-in-part of U.S. patent application Ser. No. 09/635,892, now U.S. Pat. No. 6,615,079, entitled, "Transdermal drug delivery and analyte extraction," filed Aug. 10, 2000, which is a divisional based on U.S. patent application Ser. No. 09/189,170 (now U.S. Pat. No. 6,148,232), filed Nov. 9, 1998, entitled, "Transdermal drug delivery and analyte extraction." Both of these applications share common inventorship with the inventorship of the present patent application and are incorporated herein by reference.

FIELD OF THE INVENTION

The present invention relates generally to methods and devices for drug delivery and analyte extraction, and specifically to medical methods and devices for puncturing the outer layer of living skin and to methods and devices for transdermal drug delivery and analyte extraction.

BACKGROUND OF THE INVENTION

A number of different methods have been developed to perform transdermal drug delivery and/or analyte extraction, including passive diffusion of a drug or analyte between a skin patch and skin, as well as active processes such as iontophoresis, sonophoresis, electroporation, and chemically enhanced diffusion. These methods are primarily used for generating transdermal movement of small molecules, but generally do not enhance the motion of large molecules through the 10–50 micron thick outermost layer of the skin, the stratum corneum epidermidis.

In an article, "Micromachined needles for the transdermal delivery of drugs," IEEE 11th Annual International Workshop on Micro-Electro-Mechanical Systems (1998), pp. 494–498, which is incorporated herein by reference, Henry et al. discuss a method of mechanically puncturing the skin with microneedles in order to increase the permeability of skin to a test drug. In the article, microfabrication techniques are described to etch an array of needles in silicon, and experiments performed on cadaver skin with the needle array demonstrated an increase in permeability subsequent to puncture of the skin. The needles are created with a predetermined length, and penetrate to the same depth from the skin surface, regardless of the local thickness of the stratum corneum. It is known that if the needles are longer than the local thickness, then the underlying epidermal tissue may be injured, while if the needles are too short, channel formation through the stratum corneum may be incomplete.

U.S. Pat. Nos. 4,775,361, 5,165,418, and 5,423,803, and PCT Publication WO 97/07734, the disclosures of which are incorporated herein by reference, describe methods of using laser pulses to locally heat the stratum corneum to about 120° C., thereby causing local ablation, in order to cause a single hole to develop in the stratum corneum through which large molecules may pass. Whereas some selectivity of ablation depth can be attained by varying the wavelength of the laser pulse, no feedback mechanism is disclosed whereby the laser pulses are terminated upon generation of the necessary damage to the stratum corneum.

PCT Publication WO 97/07734 also discloses thermal ablation of the stratum corneum using an electrically resistive element in contact with the stratum corneum, such that a high current through the element causes a general heating of tissue in its vicinity, most particularly the stratum corneum. As above, no means are disclosed to terminate current flow upon sufficient disruption of the stratum corneum. Additionally, thermal characteristics of skin vary highly across different areas of an individual's skin, as well as among a group of subjects, making optimal thermal dosages, which produce the desired ablation without causing pain, very difficult to determine. Lastly, increasing transdermal molecular flow by increasing the permeability of the stratum corneum, whether using microneedles, laser energy, or resistive heating of tissue, is inherently a two step process: (a) position apparatus to generate holes, and (b) apply a patch to the skin, through which the molecules will flow.

Electroporation is also well known in the art as a method to increase pore size by application of an electric field. This process is described in an article by Chizmadzhev et al., entitled "Electrical properties of skin at moderate voltages," Biophysics Journal, February, 1998, 74(2), pp. 843–856, which is incorporated herein by reference. Electroporation is disclosed as a means for transiently decreasing the electrical resistance of the stratum corneum and increasing the transdermal flux of small molecules by applying an electric field to increase the size of existing pores. Electroporation generally does not produce pores of sufficient diameter to pass large molecules therethrough. Additionally, optimal voltage profiles are difficult to determine because of naturally occurring variations as described hereinabove, as well as the lack of an accurate feedback mechanism to indicate achievement of the desired pore enlargement. If excessive voltage is applied, an irreversible breakdown occurs, resulting in damage to the skin and possible sensations of pain.

U.S. Pat. No. 5,019,034 to Weaver et al., whose disclosure is incorporated herein by reference, describes apparatus for applying high voltage, short duration electrical pulses on the skin to produce electroporation, and states that " . . . reversible electrical breakdown . . . along with an enhanced tissue permeability, is the characteristic effect of electroporation."

SUMMARY OF THE INVENTION

It is an object of some aspects of the present invention to provide improved apparatus and methods for transdermal delivery of an active substance.

It is a further object of some aspects of the present invention to provide improved apparatus and methods for transdermal analyte extraction.

It is yet a further object of some aspects of the present invention to provide improved apparatus and methods for creating narrow channels through the stratum corneum of living skin by puncturing.

It is still a further object of some aspects of the present invention to provide improved apparatus and methods for reducing sensation and minimizing damage to skin underlying the stratum corneum during channel creation.

It is an additional object of some aspects of the present invention to provide improved apparatus and methods for controlling the timing of channel creation.

It is yet an additional object of some aspects of the present invention to provide improved apparatus and methods for regulating channel creation responsive to properties of the skin.

It is another object of some aspects of the present invention to provide improved apparatus and methods for puncturing the skin and/or transdermally delivering an active substance and/or transdermally extracting an analyte, using a miniature, self-contained device.

It is yet another object of some aspects of the present invention to provide improved apparatus and methods for transdermally delivering an active substance using a standard medical skin patch.

In preferred embodiments of the present invention, a device for enhancing transdermal movement of a substance comprises: (a) a skin patch, with at least two electrodes in contact with the skin of a subject; and (b) a control unit, coupled to the patch, which causes a current to pass between the electrodes through the stratum corneum epidermidis, in order to generate at least one micro-channel in the stratum corneum to enable or augment transdermal movement of the substance. Preferably, the control unit comprises switching circuitry to control the magnitude and/or duration of the electric field at the electrode.

The term "micro-channel" as used in the context of the present patent application and in the claims refers to a pathway generally extending from the surface of the skin through all or a significant part of the stratum corneum, through which pathway molecules can diffuse. Preferably, micro-channels allow the diffusion therethrough of large molecules at a greater rate than the same molecules would diffuse through pores generated by electroporation. It is believed that such micro-channels are formed due to local power dissipation leading to ablation of the stratum corneum when an electric field of sufficient magnitude is applied to a small area of the skin, in contact with the electrodes, for a certain period of time. Unlike methods of electrically-promoted drug delivery known in the art, such as iontophoresis and electroporation, the present invention enables relatively large channels to be formed, through which even large molecules of the active substance can pass rapidly, without the necessity of ionizing or polarizing the molecules.

The current flow between the electrodes can be described as having two components: (a) a perpendicular component, which is generally perpendicular to the skin surface (and, if the associated electric field is sufficiently large, may cause current to go through the stratum corneum into the underlying epidermal tissue and dermis); and (b) a lateral component, generally parallel to the skin surface, which remains generally within the stratum corneum. Substantially all of the current generated at one electrode ultimately emerges from the skin and is taken up by an adjacent electrode.

In preferred embodiments of the present invention, methods and/or apparatus are employed to increase the relative value of the lateral component with respect to the perpendicular component. In general, the stratum corneum epidermidis (the superficial layer of the epidermis) demonstrates a significantly higher resistance to the passage of molecules therethrough than does the underlying epidermal tissue. It is therefore an object of these preferred embodiments of the present invention to form micro-channels in the stratum corneum by ablating the stratum corneum in order to increase conductance of the substance therethrough, and to generally not directly affect or damage epidermal tissue underlying the stratum corneum or in the innervated dermis. Additionally, limiting current flow substantially to the non-innervated stratum corneum is expected to decrease or eliminate the subject's sensations, discomfort, or pain responsive to use of the present invention, particularly as compared with other procedures known in the art.

A voltage applied between two electrodes on the skin generates an electric field that is to a large extent confined to the volume in a vicinity of the electrodes. Thus, electrodes which are widely spaced produce a field—and current flow responsive thereto—which extends relatively deep into the skin. Conversely, electrodes which are closely spaced do not generate significant current flow at deeper layers. Therefore, in some preferred embodiments of the present invention, the electrodes of the device are separated by distances smaller than about 100 microns (but for some applications by distances of up to approximately 500 microns), in order to generate a current flow which is largely confined to a thin layer, comprising most or all of the stratum corneum. This effectively results in a desired larger value of the ratio of the lateral component to the perpendicular component, as described hereinabove.

In some of these preferred embodiments of the present invention, a high-frequency AC current with an optional DC current added thereto is applied between the closely-spaced electrodes in order to generate lateral capacitive currents in the stratum corneum and to cause breakdown and micro-channel formation in the stratum corneum.

In some preferred embodiments of the present invention, the patch comprises an array of electrodes, preferably closely-spaced electrodes, which act together to produce a high micro-channel density in an area of the skin under the patch. Preferably, the control unit and/or associated circuitry sequentially or simultaneously evaluates the current flow through each electrode, or a subset of the electrodes, in order to determine when one or more micro-channels have formed responsive to the applied field. Responsive thereto, the control unit discontinues application of the field. Since the formation of a micro-channel is typically marked by a local drop in electrical resistance of the skin, the control unit may, for example, reduce the voltage or current applied at any electrode wherein the current has exceeded a threshold. By reducing current flow upon or shortly after micro-channel formation, the likelihood of skin burns or pain sensations is minimized.

In some preferred embodiments of the present invention, a relatively high voltage is applied to the electrodes initially, so as to induce formation of micro-channels through the skin. A property of the current flow is detected, and the current is reduced or terminated when the property reaches a predetermined threshold. Preferably, the detected property of the current flow is secondary to changes in a conduction property of the skin, responsive to formation of one or more micro-channels through the stratum corneum.

Alternatively or additionally, a time-varying voltage V(t), characterized, for example, by the formula $V(t)=V_0+kt^n$, is applied between a first electrode and a second electrode in the skin patch until a shut-off signal is generated. (Constants k and n are nonnegative.) Other forms of V(t) may include a sinusoid, an exponential term, or a series of pulses. A current I(t), flowing responsive to the applied field, is measured by the control unit, as described hereinabove. Calculations of the values of $\int I(t)dt$, $dI/dt$ and/or $d^2I/dt^2$ are frequently performed. Comparisons of I and/or $\int I(t)dt$ and/or $dI/dt$ and/or $d^2I/dt^2$ with respective threshold values are used as indicators of micro-channel formation and/or to determine when to generate the shut-off signal for the electrodes.

Further alternatively or additionally, in embodiments in which V(t) is sinusoidal, the control unit preferably calculates changes in a phase shift between V(t) and I(t) during application of the electric field, and controls the field responsive to these changes. It is believed that cells in the stratum corneum demonstrate capacitance, which causes the phase shift, and that ablation of the stratum corneum decreases the capacitance and is evidenced by a decrease in the phase shift.

Still further alternatively or additionally, the total charge which is passed through the skin is limited by a capacitor, inductor, or other energy-storage device. An appropriate choice of values for these components sets an absolute maximum quantity of charge which can pass through the skin, and thus limits any damage that can be caused thereby.

In some preferred embodiments of the present invention, one or more of the electrodes comprise or are coupled to an electrically conductive dissolving element, where the dissolving rate is generally proportional to the current passing through the electrode. When a sufficient quantity of charge has passed through the dissolving element, the electrode ceases to conduct electricity. Thus, a maximum total charge, $Q_{total}$, is associated with an electrode, such that current flows through the element for only as long as $q(t) \equiv \int I(t)dt < Q_{total}$. This serves as a safety feature, reducing the possibility of skin burns secondary to applied electric fields. Alternatively or additionally, the dissolving element is constructed so that it becomes non-conductive after a quantity of charge has passed therethrough which is sufficient to ablate the stratum corneum.

In some further preferred embodiments of the present invention, the electrodes are "printed" directly on the skin, preferably by stamping or by employing a transfer patch of a conductive substance (such as, for example, a conductive ink containing silver grains). In applications of such embodiments of the present invention for transdermal drug delivery, the conductive substance preferably comprises a matrix holding the drug to be administered to a subject.

Preferably, the printed electrodes demonstrate a substantially complete loss of conductance therethrough upon ablation of the stratum corneum responsive to the applied electric field. Further preferably, each printed electrode comprises a material which is conductive only when current flowing therethrough remains below a threshold value. If the current exceeds the threshold, then thermal fusion of the material causes it to become largely nonconductive, i.e. the material acts as a fuse. Still further preferably, current continues to flow through the other electrodes until they reach the threshold current, at a time which is generally associated with the time required for ablation of the stratum corneum, as described hereinabove. In some of these embodiments, the control unit may be made substantially simpler than as described regarding other embodiments, and generally does not need other circuitry in order to determine whether to generate a shut-off signal.

In still further preferred embodiments of the present invention, two electrodes on the patch form a concentric electrode pair, in which an inner electrode generates a current which passes through the stratum corneum to an outer electrode surrounding the inner electrode. The distance between the inner and outer electrodes is preferably between about 50 and about 200 microns, in order to maintain the ratio of the lateral to the perpendicular component of the current at a high value, as described hereinabove.

In some preferred embodiments of the present invention, a conductance-enhancing substance, preferably comprising a conductive cream or ink, is applied to the skin in order to increase the ratio of the lateral to the perpendicular component of current flow. Alternatively or additionally, the conductance-enhancing substance comprises a composition with a high diffusion coefficient, which diffuses into the lipid layers of the stratum corneum and further augments the selective power dissipation therein, in order to ablate the stratum corneum with substantially little damage to the underlying tissue. In some applications, the substance has an electrical charge associated therewith, such that when a small lateral field is applied, lateral diffusion of the substance within the stratum corneum is enhanced (i.e., iontophoresis of the substance).

In some of these preferred embodiments which utilize a conductance-enhancing substance, the substance further comprises an active substance, for example, a pharmaceutical product, dissolved or mixed therein. Since breakdown of the stratum corneum is often associated with removal of the enhanced conductivity path afforded by the conductance-enhancing substance, it is preferable in many of these embodiments to use a substantially constant voltage source to generate current at the electrodes. Removal of the enhanced conductivity path will result in a desired reduced power dissipation in the stratum corneum ($P=V^2/R$), since the voltage remains constant while resistance increases.

In other preferred embodiments of the present invention, ablation of the stratum corneum is accomplished using a current-limited source to power the electrodes. It is believed that the stratum corneum generally displays high electrical resistance, while epidermal tissue underlying the stratum corneum has significantly lower electrical resistance. Ablation of the stratum corneum (i.e., removal of the high-resistance tissue) is therefore associated with a net decrease of electrical resistance between the electrodes, and the power dissipated in the epidermis following electrical breakdown will decrease, typically proportional to the change in resistance ($P=I^2R$).

Monitoring changes in voltage, current, and/or phase for each electrode in the control unit may require, in certain implementations, a significant amount of circuitry. Therefore, in some preferred embodiments of the present invention, the control unit comprises one or more clusters of electrodes, in which monitoring and control are performed for each cluster rather than for the individual electrodes therein. The cluster is preferably over a relatively small area of skin, for example, from about 1 mm$^2$ to about 100 mm$^2$, in which properties of the skin are assumed to be substantially constant.

In some preferred embodiments of the present invention, the device is a stand-alone device, which enables transdermal delivery of an active substance or enhances transdermal motion of an analyte. Alternatively, the device creates micro-channels as described hereinabove and is then removed from the skin, in order to enhance the transdermal delivery of a substance into or out of a commercially-available skin patch subsequently placed on the skin. In other preferred embodiments of the present invention, the device is an add-on to commercially available transdermal drug delivery/analyte extraction devices, and serves primarily to create the micro-channels in the stratum corneum, and optionally to act as a vehicle through which the substance may pass.

In some preferred embodiments of the present invention, handheld apparatus for transdermal drug delivery and/or analyte extraction comprises a handle or other housing, a control unit, electrodes, and an ablation surface. The apparatus is passed by the user over a selected region of the skin, such that the electrodes on the ablation surface ablate the stratum corneum. Preferably, the ablation surface is coupled to a wheel which rotates as it moves across the skin, causing the electrodes to repeatedly come into contact and out of contact with the skin. Alternatively, the ablation surface slides across the skin without the use of a wheel, such that some electrodes substantially continuously maintain contact with the skin as the ablation surface moves along the skin.

Preferably, the handheld apparatus comprises a mechanical disposition sensor, coupled to send a disposition sensor signal to the control unit responsive to motion of the apparatus. In a preferred embodiment, the mechanical disposition sensor comprises a linear or angular accelerometer. Preferably, the control unit controls current flow to one or more pairs of the electrodes based at least in part on information including the position or motion of the ablation surface. For some applications, the control unit assesses the speed of the handheld apparatus, as determined by the disposition sensor and informs the user whether the present speed is appropriate for proper operation of the apparatus.

Alternatively or additionally, the mechanical disposition sensor comprises a linear or angular position sensor. For applications in which the ablation surface is coupled to a freely-rotating wheel, the output of the angular position sensor is preferably used to indicate to the control unit when to pre-charge one or more capacitors which convey current to the electrodes, typically at a desired interval before the electrodes contact the skin. This technique may advantageously be used to improve the efficiency of the handheld apparatus by optimizing the utilization of a battery of the apparatus.

In a preferred embodiment, the handheld apparatus comprises an output unit coupled to the control unit, to enable the control unit to communicate pertinent information to the user. Preferably, the information comprises some or all of the following:

the operational status of the device, an indication following successful ablation of the stratum corneum by one or more pairs of electrodes, the number of micro-channels formed in the current application of the device, and the amount of skin surface treated by the device.

In a preferred embodiment the output unit comprises a display, such as an LCD. Alternatively or additionally, the output unit comprises a speaker, preferably enabled to convey some of the information.

In some preferred embodiments, the handheld apparatus ablates the stratum corneum so as to prepare the skin for drug delivery or analyte extraction by a separate drug delivery unit or analyte extraction unit. For example, a standard skin patch containing a drug could be applied to the region of skin ablated by the handheld apparatus. Because ablation of the stratum corneum as provided by these embodiments typically produces essentially no sensation, the handheld apparatus preferably comprises means for demarcating the region of skin prepared by the device. The demarcation enables the user to place the drug delivery unit or analyte extraction unit on the correct region of skin. For example, the device may comprise an ink or dye reservoir and means for delivering the ink or dye to the surface of the skin region which was treated by the device.

In other preferred embodiments, the handheld apparatus is used both to prepare the skin for drug delivery and to deliver the drug to the surface of the prepared skin. Preferably, the handheld apparatus comprises a drug reservoir and means for delivering the drug to the surface of the skin. For example, a porous material may be placed between adjacent electrodes, and coupled to the drug reservoir by a conduit such that the drug can flow from the reservoir, through the porous material, to the skin. Typically, the porosity of the material is selected so as to transfer the drug to the skin at a desired rate.

Alternatively or additionally, the drug reservoir comprises a pressure sensor, a sensor for determining the amount of drug in the reservoir, and a pump coupled to the control unit. Typically, the control unit drives the pump, responsive to a signal from the pressure sensor and responsive to pre-programmed parameters, so as to control the rate and/or quantity of drug transferred to the ablated portion of the skin. In some preferred embodiments, the control unit actuates the display to show messages related to this process, e.g., "Delivering drug," "Delivery completed," and "Reservoir empty. Please refill."

In another preferred embodiment, a pre-moistened patch containing the requisite amount of drug is affixed to the ablation surface before use. For example, a standard medical patch may be attached to the ablation surface, in a manner that allows the electrodes to protrude through the patch. After one use, the patch is typically discarded.

In a preferred embodiment, an application surface for applying the drug is coupled to the handle of the handheld apparatus. Preferably, the application surface is behind the ablation surface as the handheld apparatus is passed over the skin, such that drug stored in or near the application surface is conveyed to the ablated skin during the motion of the handheld apparatus. For example, the application surface may comprise a drug reservoir, a conduit and a porous material, affixed to the handheld apparatus, such that the porous material is held in contact with the skin behind the ablation surface. In this manner, the porous material delivers the drug to the ablated region as the apparatus is passed over the skin. Preferably, the application surface is held in contact with the skin, such that the porous material slides across the skin. Alternatively, the application surface is coupled to a wheel, such that the porous material rolls across the skin.

In a preferred embodiment, the drug is pre-applied to an adhesive strip which is rolled, sometimes several times, around a spool attached to the handle of the handheld apparatus. Preferably, the spool is behind the ablation surface, such that as the handheld apparatus is moved across the skin, the adhesive strip unrolls and adheres to the region of skin which was just ablated. In this manner, the drug on the strip is brought in contact with the ablated region of the skin. Preferably, a desired quantity of the drug is uniformly applied to the adhesive strip. Alternatively, the drug is applied at discrete points on the adhesive strip, and the adhesive strip is so aligned on the spool such that the drug is placed directly over the individual ablated areas in the stratum corneum. A preferred technique for aligning the drug-delivery spool with the ablation surface includes attaching the spool and the ablation surface to the handle with the aid of alignment pins and/or notches, such that the discrete regions where the drug occurs on the adhesive strip are automatically unrolled onto the ablations in the stratum corneum.

There is therefore provided, in accordance with a preferred embodiment of the present invention, a device for treating skin on the body of a subject, including:

a plurality of electrodes, which are adapted to be placed in contact with the skin and then moved across the skin while maintaining electrical contact with the skin; and a power source, which is adapted to apply a current between two or more of the plurality of electrodes at the same time as the electrodes are being moved across the skin.

Typically, the power source is adapted to apply the current such that skin layers beneath stratum corneum epidermidis of the skin are substantially not ablated. Moreover, the power source is also typically adapted to apply the current so as to ablate stratum corneum epidermidis of the skin. For some applications, the power source is adapted to configure the current so as to ablate both the stratum corneum and, at least partially, a layer of the skin deeper than the stratum corneum.

In a preferred embodiment, the device includes a marking unit, adapted to apply a substance to the skin so as to demarcate a region of the skin to which the current is applied. Alternatively or additionally, the device includes one or more protrusive elements, adapted to press the skin so as to demarcate a region of the skin to which the current is applied.

Preferably, at least one of the electrodes is adapted to contact the skin to create a contact area having a characteristic length of between about 10 and 100 microns.

In a preferred embodiment, at least one of the electrodes includes a bipolar electrode. Alternatively or additionally, the two or more electrodes include a return electrode and two or more current-driving electrodes, and the power source is adapted to apply respective currents between each of the current-driving electrodes and the return electrode.

Preferably, the power source is adapted to apply the current in order to allow a substance to pass through the skin. For example, the power source may be adapted to apply the current in order to allow a substance to pass through the skin into the body of the subject. Alternatively or additionally, the power source may be adapted to apply the current in order to allow a substance to pass through the skin from within the body of the subject.

Preferably, the device includes a substance application unit, adapted to apply a substance to the skin at a site on the skin to which the current is applied.

In a preferred embodiment, the substance application unit includes:

a spool, adapted to rotate as the device moves across the skin; and a substance application strip having the substance applied thereto, which strip is adapted to be disposed around the spool, so as to unwind from the spool as the device is moved across the skin, and so as to cover the site on the skin to which the current is applied.

Typically, the substance application strip includes an adhesive, adapted to hold the strip in contact with the skin.

Alternatively or additionally, the substance application unit includes:

a reservoir, adapted to contain a dose of the substance; and a conduit, coupled to the reservoir so as to transport the substance to the site.

For some applications, the conduit is adapted to provide a desired flow rate of the substance. Alternatively or additionally, the substance application unit includes a porous material, through which the substance passes during transport to the skin, so as to provide a desired flow rate of the substance.

In a preferred embodiment, the substance application unit includes a pump, coupled to the reservoir, which is adapted to provide a desired flow rate of the substance.

There is further provided, in accordance with a preferred embodiment of the present invention, a device for treating skin on the body of a subject, including:

a roller, adapted to rotate when it is moved across the skin;

a plurality of electrodes, disposed over a surface of the roller, so as to be placed in sequence into contact with the skin as the roller is moved across the skin; and a power source, which is adapted to drive a current through each electrode when the electrode is in contact with the skin.

There is still further provided, in accordance with a preferred embodiment of the present invention, a device for treating skin on the body of a subject, including:

a housing;

a plurality of electrodes, disposed on a surface of the housing, which are adapted to be placed in contact with the skin;

a motion sensor, which is adapted to generate a sensor signal responsive to motion of the housing; and a control unit, which is adapted to receive the sensor signal, to determine, responsive thereto, a physical disposition of the device, and to control current flow to the plurality of electrodes responsive to determining the physical disposition.

Preferably, the control unit is adapted to determine a velocity of the device and to control the current flow to the electrodes responsive thereto. In a preferred embodiment, the control unit is adapted to terminate the current flow if the velocity is outside of a specified operating range.

Alternatively or additionally, the control unit is additionally adapted to determine a distance traveled by the device, and to control the current flow to the electrodes responsive thereto. In a preferred embodiment, the control unit is adapted to terminate the current flow after the device has traveled a specified distance.

Further alternatively or additionally, the control unit is adapted to determine an acceleration of the device and to control the current flow to the electrodes responsive thereto. In a preferred embodiment, the control unit is adapted to terminate the current flow if the acceleration is outside of a specified operating range.

Preferably, the device includes an output unit, coupled to the control unit, and the control unit is adapted to actuate the output unit to generate an output signal indicative to the subject of the physical disposition of the device. In a preferred embodiment, the output unit includes a speaker, and the control unit is adapted to actuate the speaker responsive to the physical disposition. Alternatively or additionally, the output unit includes a display, and the control unit is adapted to actuate the display responsive to the physical disposition. There is yet further provided, in accordance with a preferred embodiment of the present invention, a device for treating skin on the body of a subject, including:

a housing;

a plurality of electrodes, disposed on a surface of the housing, which are adapted to be placed in contact with the skin and to apply a current to the skin;

a motion sensor, which is adapted to generate a sensor signal responsive to motion of the housing;

an output unit; and a control unit, which is adapted to receive the sensor signal, to determine, responsive thereto, a physical disposition of the device, and to actuate the output unit to generate an output signal indicative to the subject of the physical disposition of the device.

In a preferred embodiment, the control unit is adapted to determine a velocity or acceleration of the device, and to actuate the output unit to generate the output signal responsive to the velocity or acceleration of the device. Alternatively or additionally, the control unit is adapted to determine a distance traveled by the device, and to actuate the output unit to generate the output signal responsive to the distance traveled by the device.

There is also provided, in accordance with a preferred embodiment of the present invention, a device for causing a pharmaceutical substance to enter a bloodstream of a subject through a site on skin of the subject, including:

a housing;

a spool, coupled to the housing, which is adapted to rotate when the housing is moved across the skin; and a substance application strip having the substance applied thereto, which strip is adapted to be disposed around the spool, so as to unwind from the spool as the housing is moved across the skin, and to cover the site on the skin, such that the pharmaceutical substance travels through the skin and enters the bloodstream.

Preferably, the device includes a plurality of electrodes, adapted to apply a current to sites on the skin, wherein the substance application strip is adapted to have the substance applied to discrete sites of the strip which correspond to the sites on the skin.

In a preferred embodiment, the substance application strip is divided into sections, wherein each section has a dose of the substance applied thereto, and wherein each section is arranged to be removed from the strip following unwinding of the section from the spool.

There is also provided, in accordance with a preferred embodiment of the present invention, a method for treating skin on the body of a subject, including:

placing a plurality of electrodes in contact with the skin;

moving the electrodes across the skin while maintaining their electrical contact with the skin; and driving a current between two or more of the plurality of electrodes at the same time as the electrodes are being moved across the skin.

Preferably, driving the current includes configuring a parameter of the current such that skin layers beneath stratum corneum epidermidis of the skin are substantially not ablated by the current. Alternatively or additionally, driving the current includes configuring a parameter of the current such that stratum corneum epidermidis of the skin is ablated by the current.

In a preferred embodiment, the method includes applying a marking substance to the skin so as to demarcate a region of the skin to which the current is applied.

Driving the current includes driving the current in a bipolar mode. Alternatively or additionally, driving the current includes driving the current in a monopolar mode.

Preferably, driving the current includes configuring a parameter of the current so as to allow a substance to pass through the skin. Further preferably, the method includes delivering a substance into the skin at a site on the skin to which the current is applied. Alternatively or additionally, the method includes extracting a substance through the skin at a site on the skin to which the current is applied.

Preferably, the method includes applying an active substance to the skin at a site on the skin to which the current is applied. Applying the substance typically includes regulating a flow rate of the substance, for example, by actively pumping the substance.

There is additionally provided, in accordance with a preferred embodiment of the present invention, a method for treating skin on the body of a subject, including:

placing a plurality of electrodes in contact with the skin in sequence; and driving a current through each of the electrodes when the respective electrode is in contact with the skin.

There is yet additionally provided, in accordance with a preferred embodiment of the present invention, a method for treating skin on the body of a subject, including:

placing a plurality of electrodes in contact with the skin;

determining a physical disposition of the electrodes; and driving a current between two or more of the plurality of electrodes responsive to the disposition of the electrodes.

Preferably, driving the current includes driving the current responsive to a velocity or acceleration of the electrodes. Alternatively or additionally, driving the current includes driving the current responsive to a distance traveled by the electrodes. Preferably, the current is terminated responsive to the electrodes having moved a specified distance.

In a preferred embodiment, the method includes generating an audible or visual indication to the subject the physical disposition of the electrodes.

The method preferably includes applying a pharmaceutical substance to the skin at a site on the skin to which the current is applied.

There is still additionally provided, in accordance with a preferred embodiment of the present invention, a method for treating skin on the body of a subject, including:

placing a plurality of electrodes in contact with the skin;

driving a current between two or more of the plurality of electrodes;

determining a physical disposition of the electrodes; and generating an output signal indicative to the subject of the physical disposition of the electrodes.

Preferably, generating the output signal includes generating the signal responsive to a velocity or acceleration of the electrodes. Alternatively or additionally, generating the output signal includes generating the signal responsive to a distance traveled by the electrodes.

Preferably, generating the output signal includes generating an audible or visual signal.

There is yet additionally provided, in accordance with a preferred embodiment of the present invention, a device for treating skin on the body of a subject, including:

a plurality of receiving electrodes, which are adapted to be placed in contact with the skin so as to provide electrical contact with the skin;

a driving electrode, which is adapted to be passed across the receiving electrodes so as to create electrical contact with a first one of the receiving electrodes prior to creating electrical contact with a second one of the receiving electrodes; and a power source, which is adapted to drive the driving electrode to apply a first current to the first receiving electrode when the driving electrode is in electrical contact with the first receiving electrode, and to apply a second current to the second receiving electrode when the driving electrode is in electrical contact with the second receiving electrode.

Preferably, the device includes a patch, fixed to the receiving electrodes, which patch is adapted to be applied to the skin.

In a preferred embodiment, at least one of the receiving electrodes includes a monopolar electrode.

Typically, the power source is adapted to drive the driving electrode to apply the first current at a magnitude sufficient to ablate stratum corneum of the skin.

The power source is also typically adapted to drive the driving electrode to apply the first current through the first receiving electrode into a site on the skin, and wherein the device includes a substance application unit, adapted to apply a substance to the skin at the site.

The present invention will be more fully understood from the following detailed description of the preferred embodiments thereof, taken together with the drawings in which:

BRIEF DESCRIPTION OF THE DRAWINGS

FIG. 16 is a schematic pictorial illustration of handheld apparatus for transdermal transport of a substance, in accordance with an additional preferred embodiment of the present invention.

DETAILED DESCRIPTION OF PREFERRED EMBODIMENTS

Figure 1A:
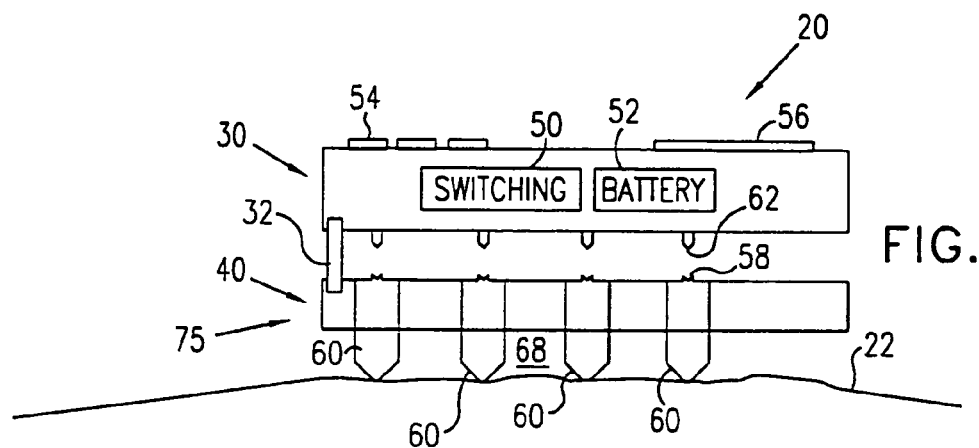
FIG. 1A is a schematic, partly sectional illustration of a device for transdermal transport of a substance, in accordance with a preferred embodiment of the present invention.

FIG. 1A is a schematic, partly sectional illustration of a skin puncturing device 20 for transdermal delivery of an active substance and/or transdermal extraction of an analyte, in accordance with a preferred embodiment of the present invention. Device 20 comprises a control unit 30 attached to a skin patch 40, which is preferably fixed to a suitable area of a subject's skin 22. Device 20 preferably administers an active substance through the normally substantially-impermeable stratum corneum layer of the skin by passing a controlled electric current therethrough, thereby ablating the stratum corneum and generating micro-channels through which the substance can pass. Alternatively or additionally, device 20 is used to generate micro-channels in the stratum corneum in order to allow passage of molecules to patch 40 from the underlying tissue, generally for diagnostic purposes.

When device 20 drives current through the stratum corneum, this tissue is heated resistively, so that when a sufficient quantity of energy has passed therethrough in a short time period, the tissue is ablated by the total energy dissipated therein. This ablation creates the desired micro-channels, i.e. physical gaps in the tissue. It has been found that application of a current to a small area of the skin leads to formation of such micro-channels, through which even large molecules can pass relatively freely, without the necessity of ionizing or polarizing the molecules, and without causing pain or substantial trauma to the dermis and epidermal tissue underlying the stratum corneum.

Control unit 30 preferably comprises a switching unit 50, a battery 52 (such as a lithium coin cell battery), and an optional user-interface comprising buttons 54 and a sensible signal generator 56, which may comprise a display and/or a buzzer. In a simplest embodiment, buttons 54 initialize and terminate analyte extraction or delivery of the active substance, although buttons 54 preferably also programmably control extraction or dosage rate and duration.

Patch 40 comprises two or more electrodes 60, preferably an array 75 of electrodes, which pass current into and out of the skin. In applications of device 20 for transdermal drug delivery, when a micro-channel has formed responsive to current flow between the electrodes, the active substance stored in patch 40 flows therethrough. In the patch, the active substance is preferably stored in or applied to inter-electrode regions 68 and flows directly therefrom into the micro-channels created in the skin.

Control unit 30, containing switching unit 50 and battery 52, is preferably designed for repeated use, to be removably attached to disposable skin patch 40. Before use, control unit 30 is fitted onto patch 40, and a protective tab (not shown) on the lower surface of patch 40 is preferably removed, exposing the one or more electrodes 60, and, in drug delivery systems, the active substance. One or more optional alignment pins 32 are preferably incorporated into control unit 30 and/or skin patch 40 to maintain proper alignment therebetween. Fitting control unit 30 to patch 40 also couples electrical contacts 62 on a lower surface of control unit 30 with electrical contacts 58 on an upper surface of skin patch 40. In some other preferred embodiments of the present invention (not shown), control unit 30 and skin patch 40 are constructed as one integrated unit.

Figure 1B:
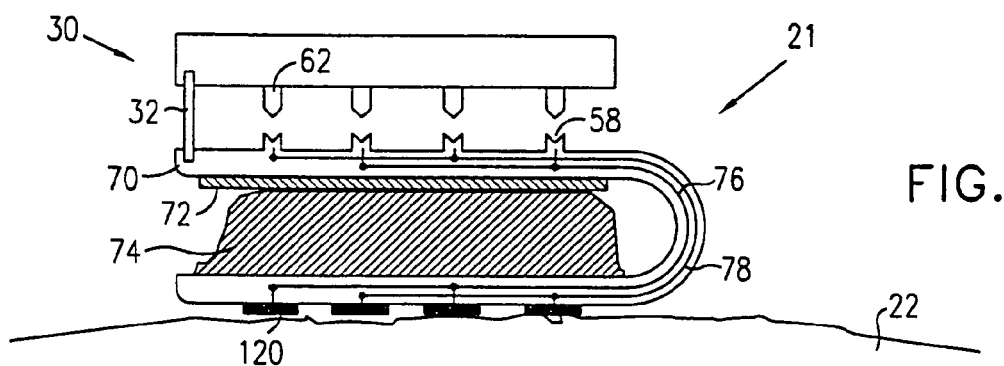
FIG. 1B is a schematic, partly sectional illustration of another device for transdermal transport of a substance, in accordance with a preferred embodiment of the present invention.

FIG. 1B is a schematic, partly sectional illustration of another device 21 for transdermal transport of a substance, in accordance with a preferred embodiment of the present invention. Device 21 operates in substantially the same manner as device 20, described hereinabove, but device 21 is preferably used in an add-on configuration with commercially available medical patches. Typically, a medical patch 74 is coupled to a porous, thin, flexible, and disposable electrode patch 70, which is used to create micro-channels in skin 22 so as to enable enhanced flow of an active substance stored within medical patch 74 through electrode patch 70 and into skin 22.

Electrode patch 70 is preferably constructed such that electrical contacts 58 thereof are coupled to electrical contacts 62 of control unit 30 and carry charge through flexible leads 76 and 78 internal to patch 70, in order to create an electric field between electrodes 120 placed against the surface of skin 22. Prior to use, medical patch 74 is placed onto electrode patch 70, typically on the opposite side of patch 70 from electrodes 120. An adhesive on the underside of medical patch 74 preferably secures the two patches together. Subsequently, electrode patch 70 is folded over, as shown in FIG. 1B, such that an upper surface of patch 74 is secured through an adhesive 72 to electrode patch 70. During operation of device 21, the active substance preferably diffuses from the lower surface of patch 74 into, and then through, patch 70 into skin 22. Device 21 is thus compatible with a broad range of currently available active or passive medical patches, which are typically of the same general construction (thin shell, internal reservoir of active substance, porous and adhesive-coated undersurface).

It is understood, of course, that device 21 as described is only one of many ways to implement some aspects of the present invention. Alternatively, for example, electrode patch 70 is not folded over; instead, control unit 30 is placed next to medical patch 74 on top of electrode patch 70. Further alternatively, control unit 30 has electrical contacts on its upper surface to which are coupled the electrical contacts of the electrical patch.

Figure 2:
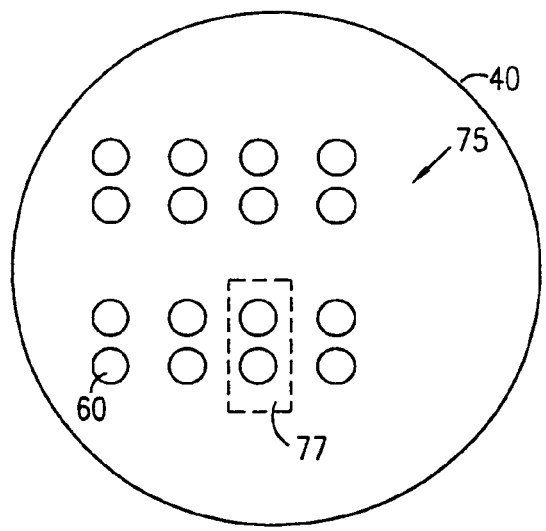
FIG. 2 is a schematic bottom view of the device of FIG. 1A, in accordance with a preferred embodiment of the present invention.

FIG. 2 is a schematic bottom view of skin patch 40 from FIG. 1A, showing array 75 of electrodes 60, in accordance with a preferred embodiment of the present invention. Although array 75 as shown comprises sixteen electrodes, it is understood that in some implementations the array might be smaller, while in others the array might be larger, for example 50×50 or even more, so as to enable a greater amount of the active substance to be delivered or analyte to be extracted. Electrodes 60 in this embodiment are preferably organized into eight electrode sets 77, such that most of the charge leaving one electrode in a set goes to the other electrode in that set, and generally does not go to electrodes in an adjacent set. Electrode sets 77 are further preferably densely packed in order to maximize the transdermal transfer rate. By way of illustration and not limitation, the density may range from 4–100 electrode sets/cm$^2$. Each electrode set typically generates at least one micro-channel before a threshold of current or total charge transfer is passed, responsive to which switching unit 50 preferably causes current to the electrode set to be terminated or reduced, as described herein.

Figure 3:
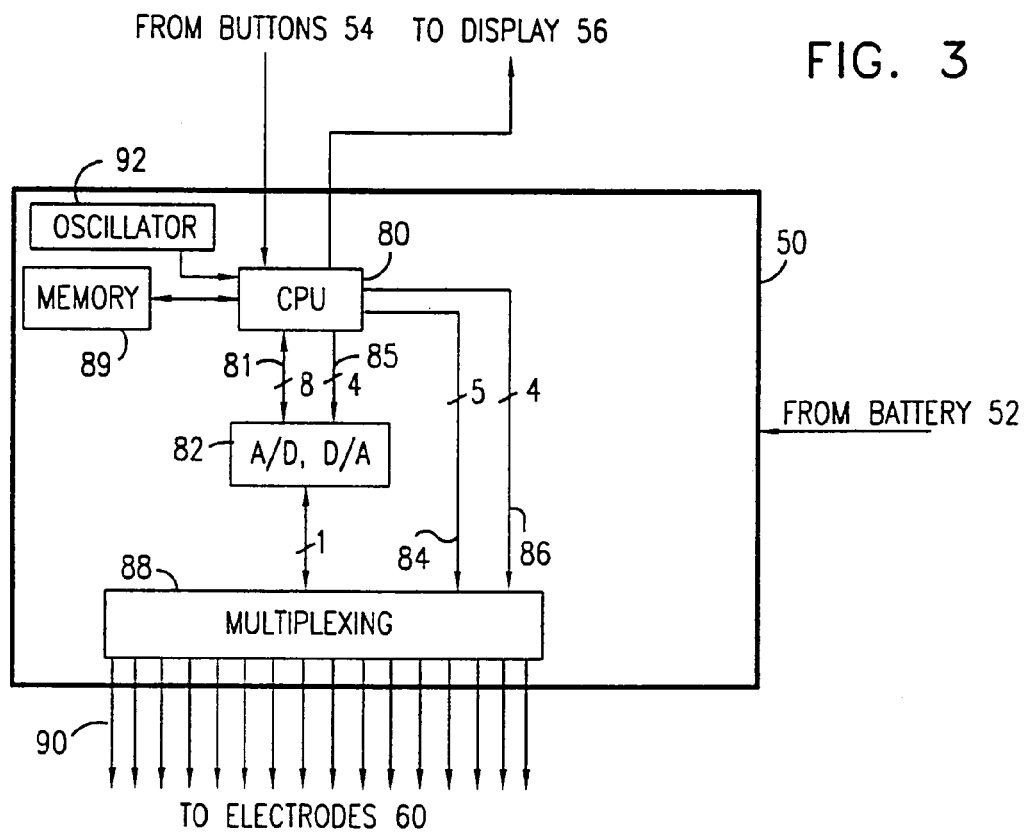
FIG. 3 is a schematic illustration of a switching unit in the device of FIG. 1A, in accordance with a preferred embodiment of the present invention.

FIG. 3 is a schematic illustration of switching unit 50 in device 20 of FIG. 1A, configured to control a 4×4 array of electrodes 60, as in FIG. 2, in accordance with a preferred embodiment of the present invention. Switching unit 50 preferably comprises a CPU 80 which actively controls the voltage V(t) applied to sixteen conductors 90 leading to electrodes 60. CPU 80 monitors the current flow, I(t), through each of conductors 90 leading to electrodes 60 in order to determine whether a characteristic of the current (e.g., time-integrated current, I, dI/dt, d$^2$I/dt$^2$) has surpassed a threshold, indicating micro-channel formation. The CPU terminates current flow to any electrode for which the threshold has been surpassed. Alternatively or additionally, in some applications, some of electrodes 60 are generally not used to initiate channel formation, but serve primarily to allow CPU 80 and/or other circuitry to monitor electrical properties of skin 22.

CPU 80, which receives a clock signal from an oscillator 92, preferably communicates with and controls electrodes 60 through eight data lines 81 and four control lines 85 which lead to an A/D-D/A converter 82, and by five address lines 84 and four control lines 86 which lead to a multiplexing unit 88. It will be understood by one skilled in the art that there are many methods to monitor and control current through a plurality of conductors, and that using a CPU, A/D-D/A converter and multiplexing unit as described herein is just one of these. Generally, data lines 81 carry in alternation a low byte and a high byte of data between the CPU and A/D-D/A converter 82. Typically, 10 bits of data, representing a desired voltage for one of the sixteen electrodes, are converted to an analog voltage in A/D-D/A converter 82, and this voltage is passed by multiplexing unit 88 to an appropriate electrode, the electrode selection being determined by the binary values represented in address lines 84. In many applications, fewer than 10 bits are required to define voltages for the respective electrodes, and circuitry within switching unit 50 is accordingly simpler.

Intermittently, CPU 80 enters a current-sensing mode, wherein switching unit 50 continues to drive current through conductors 90, but the CPU changes the state of control lines 85 and 86 in order to measure the current flow through conductors 90. Responsive to the change in control lines 86, multiplexing unit 88 measures a current through one of conductors 90, converts this measurement to a voltage, and passes the voltage to A/D-D/A converter 82 which in turn passes the digital value representing the current to the CPU. Preferably, CPU 80 scans through each of the sixteen electrodes, detects a present current flow value, stores this value in an optional memory unit 89, optionally compares the value with prior values for the same electrode in order to calculate $\int I(t)dt$, dI/dt and/or d$^2$I/dt$^2$, and regulates the potential of that electrode responsive to the current measurement and/or optional calculation. It will be understood by one skilled in the art that CPU 80, oscillator 92, and memory 89 could be replaced by other circuitry able to perform generally the same functions.

Figure 4:
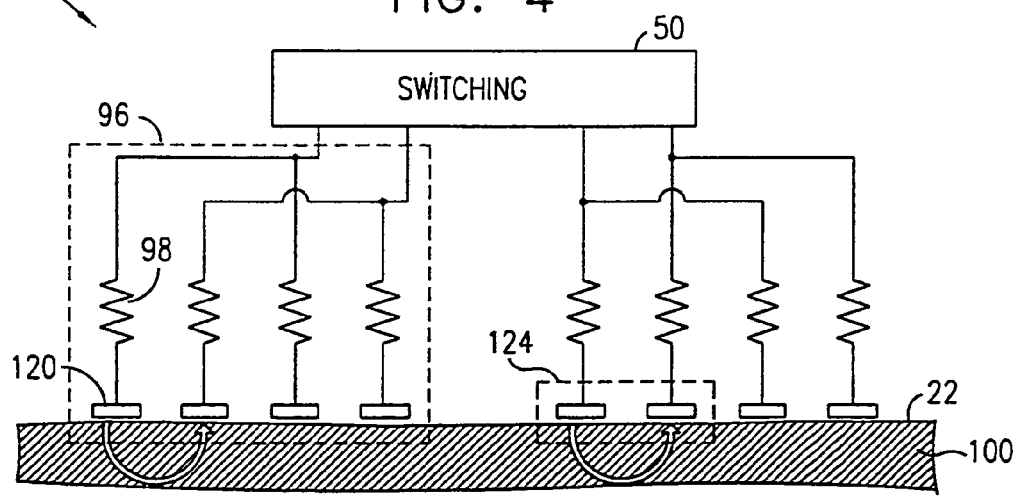
FIG. 4 is a schematic illustration of an electrode assembly, in accordance with a preferred embodiment of the present invention.

FIG. 4 is a schematic illustration of an electrode assembly 94, comprising a plurality of electrodes 120, which are placed on skin 22 in order to generate micro-channels in the stratum corneum 100, in accordance with a preferred embodiment of the present invention. Electrodes 120 in assembly 94 are grouped in sometimes overlapping sets of two or more electrodes, forming a plurality of electrode sets 124, one of which is indicated with a dashed line in FIG. 4. Current, coming from switching unit 50, generally flows from one electrode in each electrode set to the other electrodes of the set. An arrow going between the two electrodes in set 124 indicates the preferred flow of current.

Preferably, the spacing between electrodes in each electrode set is smaller than about 0.1 mm, although for some applications it may range from (by way of illustration and not limitation) 0.1 mm to about 0.3 mm. Generally, the distance is set such that an electric field penetration depth is achieved which is substantially of the same magnitude as the thickness of the stratum corneum, so that the current mostly does not enter epidermal tissue underlying the stratum corneum. Experimental results have shown that the depth of deepest ablation is generally similar to the electrode spacing, so maintaining the spacing between about 0.01 mm and about 0.1 mm optimizes generation of micro-channels while substantially reducing damage, sensation and/or pain in the innervated dermis and in the epidermal tissue below the stratum corneum.

At any point in the skin in a vicinity of two electrodes placed thereon, the electric field generated between the electrodes can be viewed as having fundamentally two components: a component perpendicular to the skin, which generally causes current flow perpendicular to the skin; and a lateral component, which generally causes current flow parallel to the skin. At a point in the skin infinitesimally below one of the electrodes, the perpendicular component is generally large and/or greater than the lateral component. The present invention seeks generally to maximize the ratio of the lateral component to the perpendicular component at the depth corresponding to the interface between the deepest portion of the stratum corneum and the most superficial portion of the remainder of the epidermis. An electric field at the base of the stratum corneum having a relatively large lateral component generates current flow predominantly in the stratum corneum, with relatively little current flow into the underlying epidermal tissue. Thus, using methods and apparatus of the present invention, tissue ablation occurs mostly in the stratum corneum, as desired, and largely does not occur in the underlying tissue.

In some applications of the embodiment shown in FIG. 4, it is preferred to print electrodes 120 directly on skin 22, typically (a) by stamping the electrodes thereon; (b) by employing a transfer patch of a conductive substance; and/or (c) by other techniques known in the art. Switching unit 50 preferably sends current to the printed electrodes via printed ports (not shown) on the upper surface of the electrodes. In uses of the present invention for transdermal drug delivery, the conductive substance preferably contains an active substance, typically dissolved or suspended therein. Alternatively or additionally, it is desirable for the printed electrode to disconnect from the switching unit or power source at substantially the same time as ablation of the stratum corneum is completed. This "self-quenching" feature of the printed electrodes is typically achieved by controlling fabrication of the electrodes, in particular by regulating the thickness and/or chemical composition thereof. Printed electrodes comprising a silver-based emulsion ink preferably undergo thermal fusion within the ink responsive to high current flow, resulting in a decrease in electrical conduction therethrough.

As discussed hereinabove with reference to FIG. 3, switching unit 50 monitors current flow to electrodes 60 (or electrodes 120, shown in FIG. 1B and subsequent figures), and selectively terminates the flow to one or more electrodes upon a determination that ablation of stratum corneum 100 has occurred. Making reference to FIG. 4, a cluster 96 of electrodes is a grouping of electrodes 120, which are typically in very close mutual proximity, and are therefore assumed to overlie an area of skin 22 which has generally uniform properties. By way of illustration and not limitation, cluster sizes generally range from about 4 mm$^2$ to about 100 mm$^2$. Switching unit 50 preferably monitors and terminates the current flow through the electrodes in cluster 96 collectively (i.e. for all of the electrodes, not individually for each electrode). Alternatively or additionally, current through electrodes 120 in cluster 96 is determined by monitoring the current in only a subset of the electrodes, and assuming the value derived therefrom to be generally representative of current through each of the other electrodes. Upon a determination by switching unit 50 that stratum corneum 100 under cluster 96 has been ablated, the current flow to all of the electrodes in cluster 96 is substantially terminated. Monitoring of clusters of electrodes generally simplifies control circuitry associated with the invention, while not substantially decreasing the performance thereof.

Optional resistive elements 98, coupled in series between switching unit 50 and electrodes 120, limit the power dissipation in the skin following the large increase of conductivity in the epidermis associated with ablation of the stratum corneum. Typical values for resistive elements 98 range from 1 kOhm–100 kOhms, but in some applications may have values outside of this range.

Figure 5:
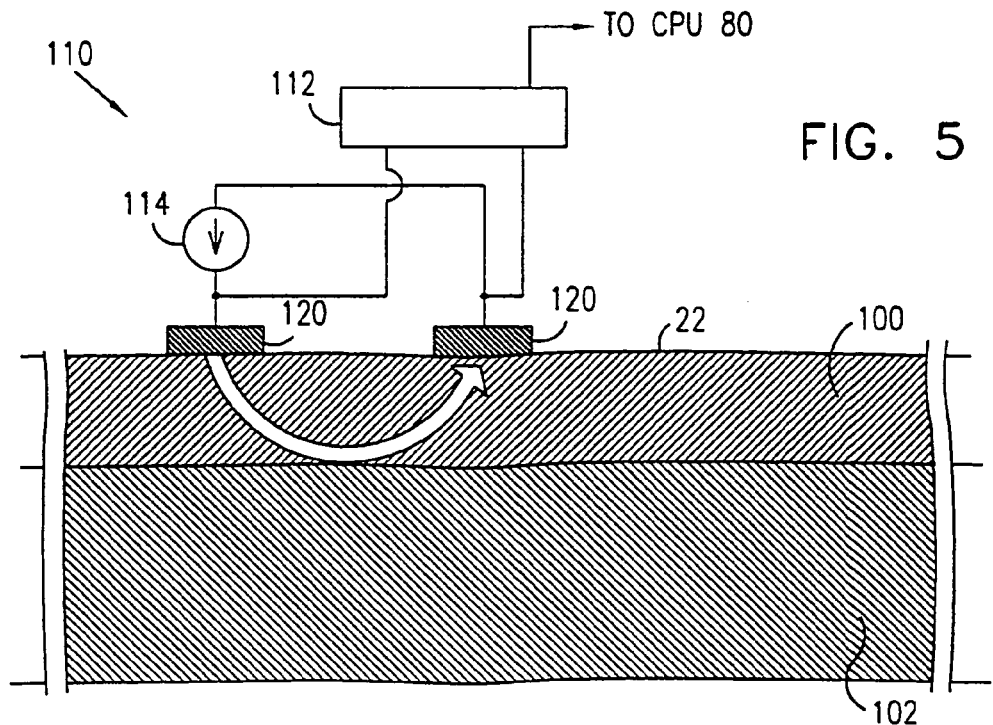
FIG. 5 is a schematic illustration of another electrode assembly, in accordance with a preferred embodiment of the present invention.

FIG. 5 is a schematic illustration of another electrode assembly 110, comprising a current source 114 coupled to drive charge through electrodes 120 on skin 22, in accordance with a preferred embodiment of the present invention. Current source 114 preferably comprises a source of electrical power (for example, a battery) connected in series with an inductive element which, due to pulse charging, exhibits properties of a current source, thereby limiting the power dissipated in underlying epidermal tissue 102 following the drop in resistance of the epidermis associated with substantially complete ablation of stratum corneum 100. Alternatively or additionally, current-limited source 114 comprises active components such as transistors, op-amps, commercially-available "ideal" current sources, etc., which maintain the current through the skin generally constant after ablation of the stratum corneum, so that the power dissipated ($P=I^2R$) will decrease with the reduced resistance of the skin upon the electrical breakdown of stratum corneum 100.

Prior to breakdown, the impedance between electrodes 120 is high, producing a generally large voltage drop therebetween, so the energy dissipated in the skin ($P=VI$) has a desired high value. The energy dissipation rate is preferably sufficient to cause electrical breakdown of stratum corneum 100 in a short time, which is typically less than 50 milliseconds, but may range from about 1 to about 1000 milliseconds. Reported values of the voltage needed to break down stratum corneum 100 spread over a range of approximately 5–1000 volts. For the purposes of the present invention, it has been found that an inter-electrode voltage of approximately 100 volts generally ablates stratum corneum 100 without causing significant damage to underlying tissue 102. It is understood, however, that for some applications or types of subjects/patients, lower or higher inter-electrode voltages may be more suitable.

Intermittently or continuously during application of the electric field to skin 22, an optional voltage sensing unit 112 preferably measures the interelectrode voltage and sends a signal corresponding thereto to CPU 80 or other circuitry in switching unit 50, which regulates the current produced by source 114 responsive to the signal. Alternatively or additionally, voltage sensing unit 112 comprises a comparator which intermittently or continuously compares the interelectrode voltage to a pre-determined threshold value, and signals source 114 when the voltage is below the threshold. In either case, the CPU, circuitry and/or comparator preferably control source 114 to reduce or terminate current flow responsive to a drop of the interelectrode voltage below the threshold value.

Figure 6:
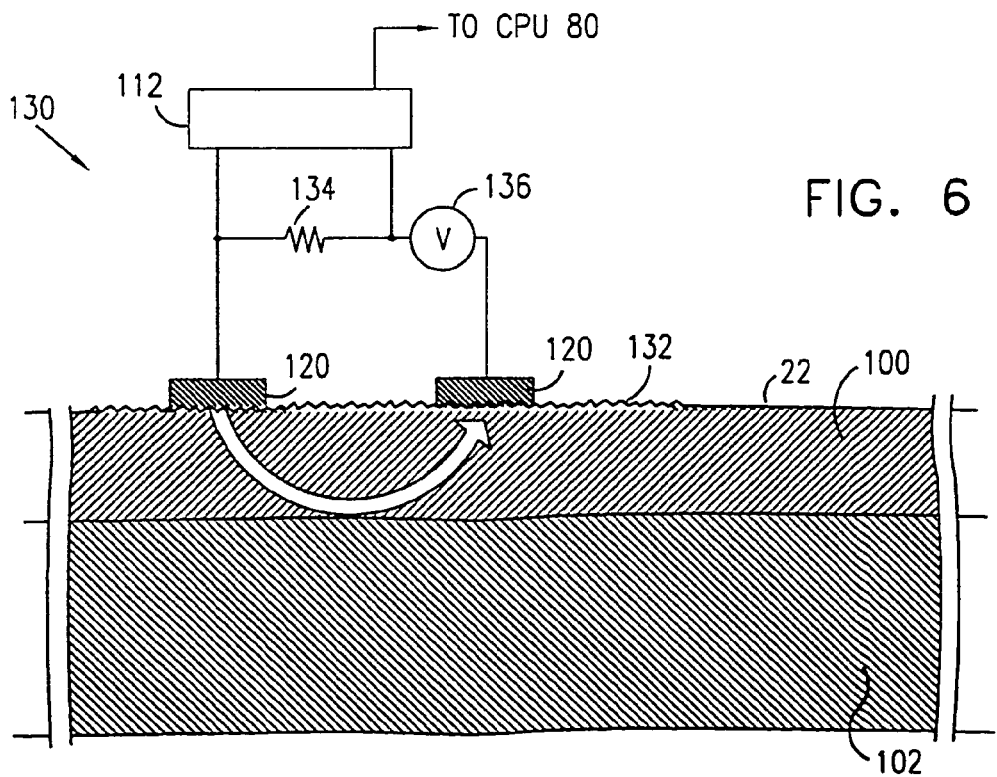
FIG. 6 is a schematic illustration of yet another electrode assembly, in accordance with a preferred embodiment of the present invention.

FIG. 6 is a schematic illustration of another electrode assembly 130, comprising a voltage source 136 coupled in series through an optional resistive element 134 to two electrodes 120 on the surface of skin 22, in accordance with a preferred embodiment of the present invention. Optional voltage sensing unit 112 measures the voltage drop across resistive element 134 in order to determine the current passing therethrough. In a manner substantially similar to that described hereinabove with reference to FIG. 5, unit 112 and/or CPU 80 and/or other circuitry in switching unit 50 regulate the output of voltage source 136 responsive to the measurement made by unit 112. Preferably, when the voltage drop across element 134 exceeds a predetermined threshold value, this is used as an indication of stratum corneum ablation and causes the voltage generated by source 136 to be reduced or terminated responsive thereto.

In applications of the embodiment shown in FIG. 6, if optional resistive element 134 and optional voltage sensing unit 112 are not used, it is preferable to employ other means for significantly reducing the current flow through electrodes 120 after micro-channel formation. This is preferably done by using "self-quenching" printed electrodes, as described hereinabove with reference to FIG. 4.

Alternatively or additionally, a conductivity-enhancing substance 132 is applied to skin 22 prior to placement of electrodes 120 thereon. Substance 132 typically improves current flow into skin 22 by decreasing the electrical resistance at the interface between electrodes 120 and skin 22. Experimental results indicate that use of substance 132 has the additional desired effect of increasing the above-mentioned ratio of the lateral component of the electric field to the perpendicular component thereof. In particular, it is believed that substance 132 diffuses into stratum corneum 100 and reduces the lateral resistance and lateral breakdown strength of the stratum corneum. By virtue of the relationship $P=V^2/R$, the increased conductivity in stratum corneum 100 (prior to the breakdown thereof) deriving from the presence of substance 132 produces a relatively high rate of energy dissipation in the stratum corneum. However, as ablation occurs, it has been observed that the enhanced conductivity path due to substance 132 is substantially removed, resulting in an increase in resistance and the desired attendant decrease in energy dissipation in the skin.

Substance 132 typically comprises a conductive cream, gel and/or ink. In some applications of this embodiment, substance 132 additionally comprises a material which has a high diffusion coefficient into the skin and promotes the increased lateral component of the electric field relative to the perpendicular component, as described hereinabove. Alternatively or additionally, "pre"-iontophoresis, using a relatively weak electric field, is used to enhance the flow of substance 132 into the outer layer of the skin before application of the stronger electric fields which create the micro-channels. The presence of the conductive substance in the skin subsequent to the pre-iontophoresis is believed to increase the rate of micro-channel creation. Pre-iontophoresis is typically implemented by applying, for example, a 3 volt DC field between the electrodes for 30 seconds in order to drive substance 132 into the skin. Alternatively or additionally, a larger AC current which produces micro-channels is supplemented by a simultaneous small DC current which supports iontophoresis of substance 132 and thereby enhances micro-channel creation.

In some applications, when micro-channels are created in order to enhance transdermal delivery of an active substance, the active substance is preferably incorporated in substance 132.

Figure 7:
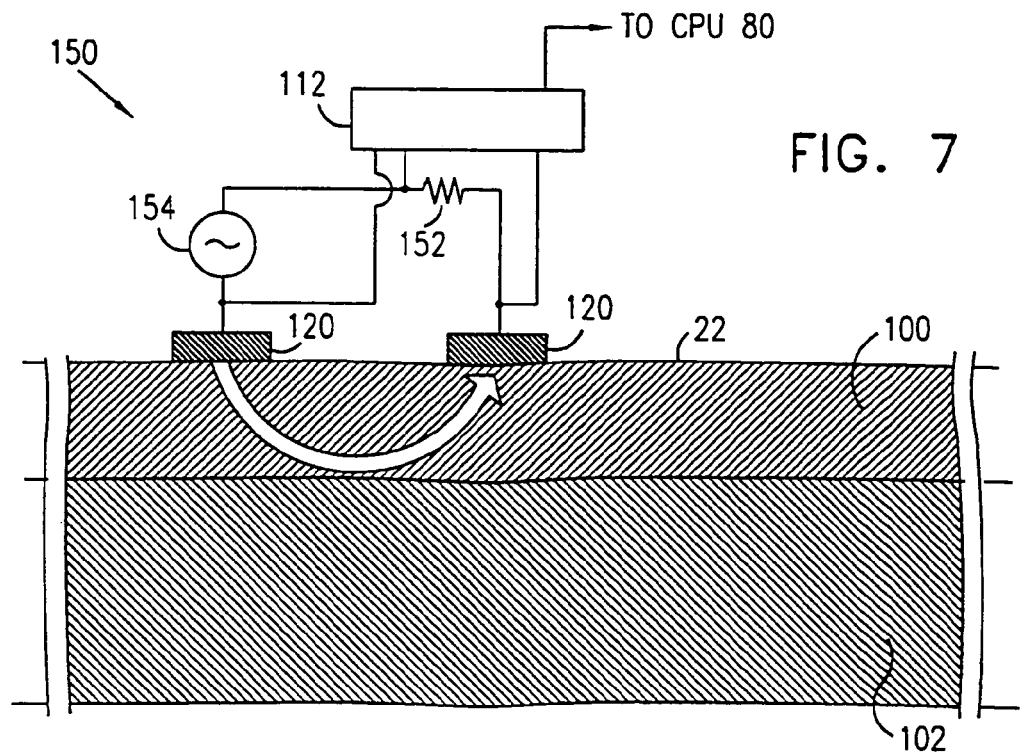
FIG. 7 is a schematic illustration of still another electrode assembly, in accordance with a preferred embodiment of the present invention.

FIG. 7 is a schematic illustration of another electrode assembly 150, comprising an AC current source 154 coupled in series with an optional resistive element 152 in order to drive current through electrodes 120 and skin 22, in accordance with a preferred embodiment of the present invention. It has been reported that the driving frequency of current through skin has a significant effect on the sensation or pain experienced by a subject. See, for example, *Principles of Applied Biomedical Instrumentation*, by L. Geddes and L. Baker, John Wiley & Sons, 1989, which is incorporated herein by reference. For the purposes of the present invention, a 10 kHz driving frequency has been found to yield good results, although any frequency between about 100 Hz and about 10 MHz is appropriate for most applications. Depending on properties of a subject's skin, it is sometimes appropriate to use driving frequencies outside of this range. Optionally, the driving frequency is cyclically modulated between two endpoints (e.g., 2 kHz and 15 kHz) during application of the electric field, such that a graph representing frequency versus time (not shown) is typically sinusoidal or triangular in character.

Stratum corneum 100 generally displays properties of a simple insulator when exposed to DC current, but displays significant capacitance under AC stimulation, particularly when the driving frequency is above 1 kHz. At these frequencies, current flow through the stratum corneum dissipates energy therein, contributing to the heating and ultimate ablation of the stratum corneum. The pre-ablation capacitance produces a measurable phase shift between the voltage across the electrodes and the current flowing therebetween, which phase shift is seen to be significantly reduced upon commencement and completion of the ablation of the stratum corneum. Sensing unit 112 is typically used to detect this phase shift by measuring the inter-electrode voltage, as described hereinabove, and by determining the current flow through electrodes 120, preferably by measuring the voltage drop across optional resistive element 152. The change of the phase shift from baseline is preferably used by sensing unit 112 and/or CPU 80 and/or other circuitry in switching unit 50 to indicate breakdown of the stratum corneum, responsive to which current flow to electrodes 120 demonstrating such a change preferably is reduced or terminated.

As described hereinabove, in some applications, substance 132 is applied to skin 22, and a DC current is superimposed on the AC current in order to cause iontophoresis of substance 132 during micro-channel creation.

Alternatively or additionally, in applications using AC and/or DC current delivery (as in FIGS. 5, 6 and 7), the duration of charge delivery is limited by means of an optional ordinary timer circuit (not shown). Further alternatively or additionally, the total charge delivered (or root mean squared charge in AC operation modes) is limited using methods known in the art. For example, energy storage components such as capacitors and/or inductors can be used to modulate charge delivery.

Although in the embodiments shown in FIGS. 5, 6, and 7, passing a threshold of current or voltage is used as an indicator of when to reduce the current applied to the skin, other functions of the current and/or voltage, such as derivatives, time-integrals, and/or powers thereof may also be evaluated in order to determine when the current should be reduced.

Figure 8A:
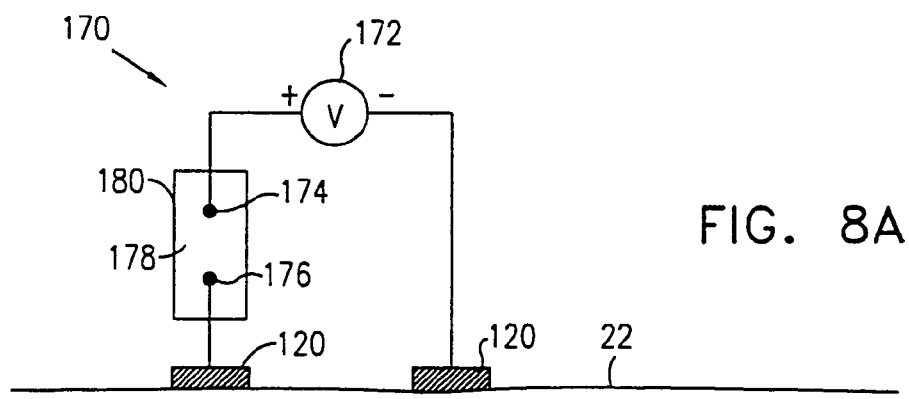
FIGS. 8A and 8B are schematic illustrations of charge-limited electrode assemblies, in accordance with preferred embodiments of the present invention.

FIG. 8A is a schematic illustration of a charge-limited electrode assembly 170, comprising an electrolyte cell 180 connected in series between a power source 172 and electrodes 120, in accordance with a preferred embodiment of the present invention. Electrolyte cell 180 comprises an anode 174 and a cathode 176, both immersed in an electrolyte solution 178, which acts as a medium for current flow from anode 174 to cathode 176. As current flows through cell 180, cathode 176 is steadily consumed by electrolysis until electrolyte cell 180 becomes substantially non-conductive. In this manner, consumption of cathode 176 progresses at a rate which is generally proportional to the current flowing therethrough. By modifying the initial mass of cathode 176, cell 180 can be built to allow a flow of charge that substantially does not exceed a predetermined value.

Figure 8B:
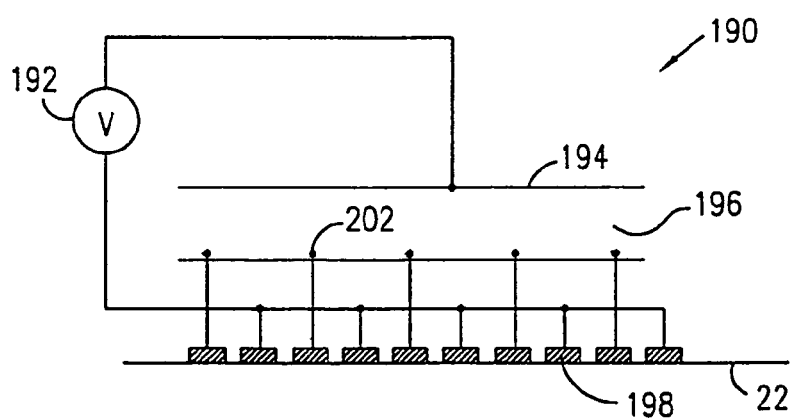

FIG. 8B is a schematic illustration of another charge-limited electrode assembly 190, comprising a power source 192 which sends current to a large-area anode 194 from which it flows through an electrolyte solution 196 to multiple cathodes 202, in accordance with a preferred embodiment of the present invention. In general, the charge-limiting functions embodied in assembly 190 are similar to those described with respect to the embodiment shown in FIG. 8A. Anode 194 comprises a fibrous material, such as paper, having fibers aligned in a generally vertical direction, perpendicular to the surface of skin 22. Alternatively or additionally, anode 194 is in very close proximity to cathodes 202, typically from about 0.1 mm to about 2 mm, in order to enhance independent termination of current through electrodes 198 coupled to cathodes 202, by reducing lateral conduction within the electrolyte solution.

Figure 9:
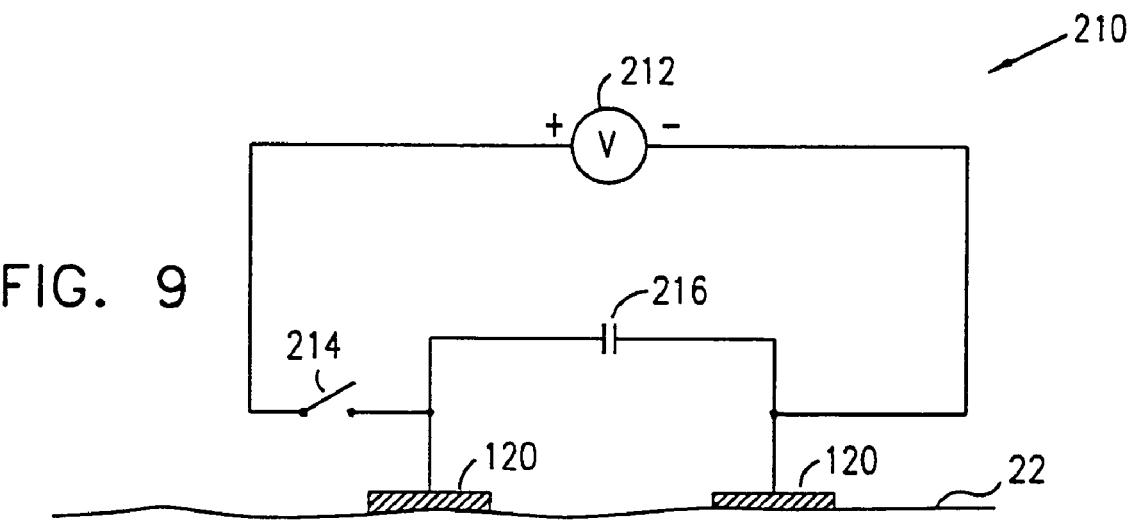
FIG. 9 is a schematic illustration of another charge-limited electrode assembly, in accordance with a preferred embodiment of the present invention.

FIG. 9 is a schematic illustration of yet another charge-limited electrode assembly 210, comprising a power source 212 in series with a controlled switch 214, in accordance with a preferred embodiment of the present invention. Source 212 and switch 214 are connected in series with a capacitor 216 across electrodes 120, which are applied to skin 22. Capacitor 216 is preferably utilized in order to limit the total charge delivered through electrodes 120 to generally not more than the charge-holding capacity of capacitor 216 at a designated voltage generated by source 212, given by the formula $q=CV$, wherein C is the capacitance of the capacitor. By way of illustration and not limitation, for an applied voltage of 50 volts, a capacitor whose capacitance ranges from about 1 nF to about 0.2 µF is appropriate.

A typical operational sequence in this preferred embodiment comprises: (a) turning on source 212; (b) closing switch 214, which results in substantially all of the current from source 212 going through and charging low-impedance capacitor 216; (c) opening switch 214 and turning off source 212; (d) allowing the discharge from capacitor 216 to drive the ablation of the stratum corneum; and (e) passively terminating the process responsive to complete discharge of capacitor 216.

Figure 10:
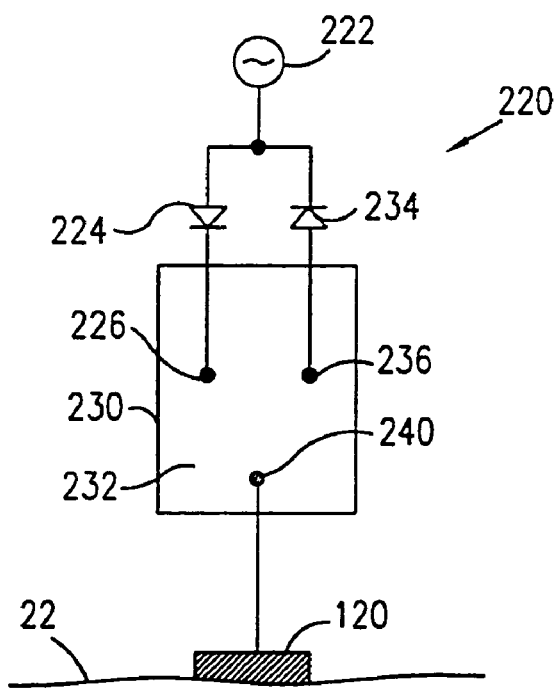
FIG. 10 is a schematic illustration of yet another charge-limited electrode assembly, in accordance with a preferred embodiment of the present invention.

FIG. 10 is a schematic illustration of still another charge-limited electrode assembly 220, comprising an AC source 222 coupled in series to an electrolyte cell 230, electrode 120, and skin 22, in accordance with a preferred embodiment of the present invention. Cell 230 preferably comprises two alternating nodes 226 and 236 and a common node 240, all nodes being immersed in an electrolyte solution 232. Except as will be described below, the function of electrolyte cell 230 is substantially similar to that of electrolytic charge-limiting devices described hereinabove with reference to FIGS. 8A and 8B.

AC source 222 produces a voltage difference across electrodes 120 (only one electrode is shown), which cycles between positive and negative phases at a pre-determined frequency, in order to provide the energy to ablate stratum corneum 100 in skin 22. During the positive phase, a diode 224 in electrolyte cell 230 passes current to cause alternating node 226 to act as an anode and common node 240 to act as a cathode, which is subsequently consumed by the electrolysis thereof during each positive phase. Conversely, during the negative phase, diode 224 blocks conduction through alternating node 226, halting the consumption of common node 240 associated with the positive phase. In a similar manner, during the negative phase, a second diode 234 passes current which allows alternating node 236 to act as a cathode (which is consumed) and common node 240 to act as an anode. When a sufficient quantity of charge has passed through electrolyte cell 230, common node 240 is completely consumed, and cell 230 becomes substantially non-conductive. Preferably, the properties of electrolyte cell 230 are determined so that the cell becomes non-conductive after passing a quantity of charge which correlates with breakdown of the stratum corneum.

Figure 11A:
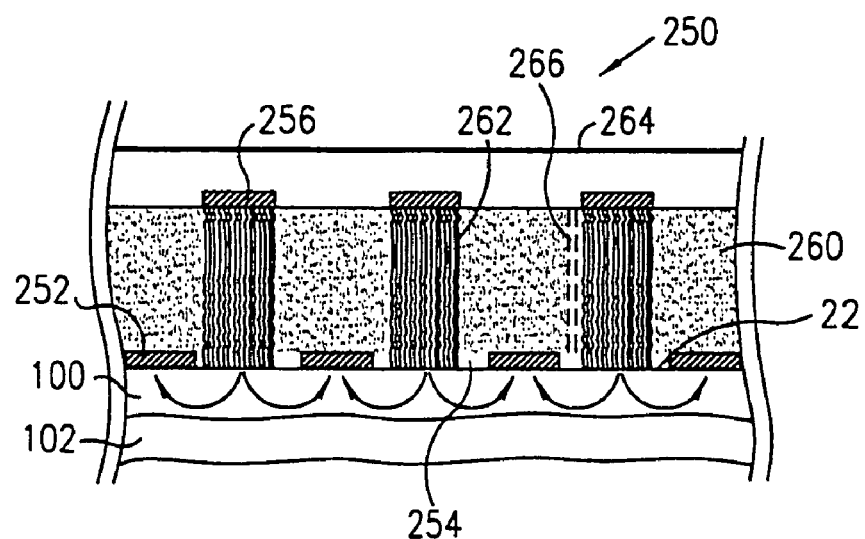
FIG. 11A is a schematic side view of a concentric electrode assembly, in accordance with a preferred embodiment of the present invention.
Figure 11B:
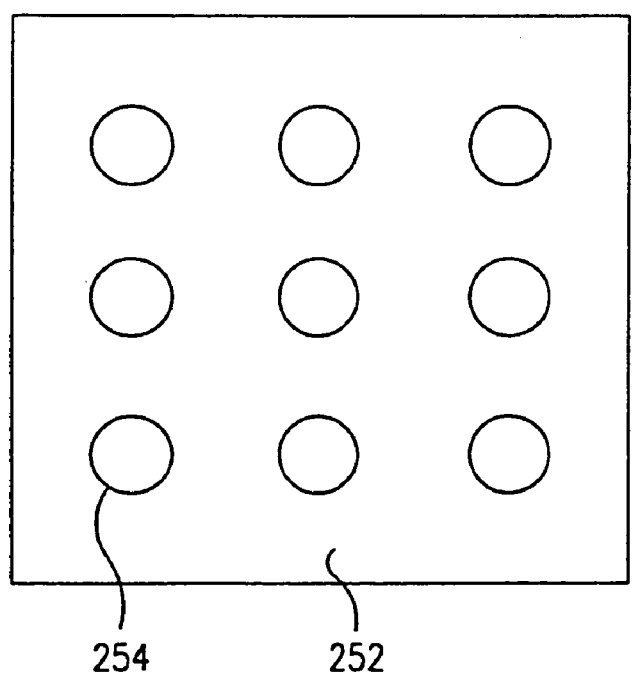
FIG. 11B is a schematic top view of a common electrode layer in the concentric electrode assembly of FIG. 11A, in accordance with a preferred embodiment of the present invention.

Reference is now made to FIGS. 11A and 11B which are, respectively, a schematic side view of a concentric electrode assembly 250 and a schematic top view of a common electrode layer 252 in assembly 250, in accordance with a preferred embodiment of the present invention. A substantially non-conductive substrate 260 overlies common electrode layer 252. Perforations 254 in layer 252 allow passage therethrough of electrodes 262, which receive charge through optional resistive members 256 from a charging bus 264 overlying substrate 260. Electrodes 262, which preferably comprise a plurality of conductive fibers, are electrically coupled to skin 22, and cause charge to pass into skin 22 and subsequently out of skin 22 through common electrode layer 252, in order to ablate stratum corneum 100.

In some preferred applications, one or more pores 266 traversing substrate 260 allow flow of active substances/analytes through substrate 260 from/to a reservoir (not shown) above substrate 260. It is noted that fabrication of concentric electrode assembly 250 is substantially similar to the process of flexible printed circuit production, which is well known in the art.

Figure 12:
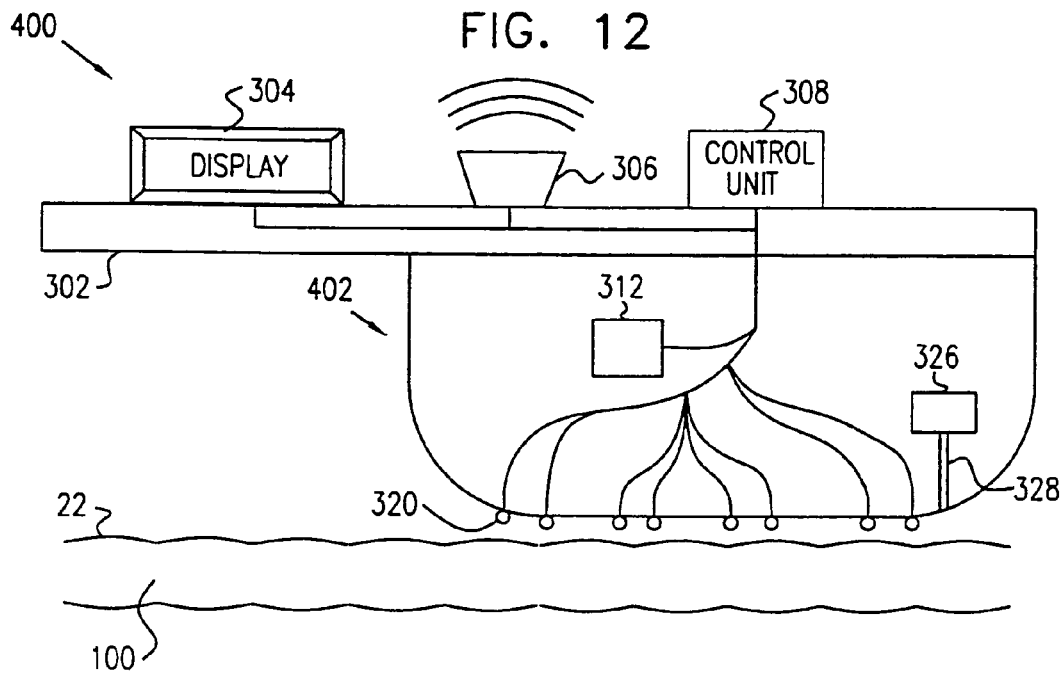
FIG. 12 is a schematic, partly sectional illustration of handheld apparatus for preparing the skin for transdermal transport of a substance, in accordance with a preferred embodiment of the present invention.

FIG. 12 is a schematic, partly sectional illustration of a handheld device 400 for ablating stratum corneum 100, prior to delivery of an active substance to skin 22 and/or extraction of an analyte from the skin, in accordance with a preferred embodiment of the present invention. Device 400 preferably comprises a handle 302, to which is attached a control unit 308, a display 304, a speaker 306, and an ablation head 402. During regular operation, the user slides ablation head 402 along the surface of skin 22, and electrodes 320 on the ablation head are driven by control unit 308 to form micro-channels in stratum corneum 100, typically using techniques described hereinabove. For example, control unit 308 may apply 1,500 volts between two of electrodes 320 for a specified amount of time, so as to drive a current determined to be sufficient to generate the micro-channels (i.e., open-loop feedback). Alternatively, control unit 308 may utilize closed-loop feedback techniques known in the art or as described hereinabove, to determine when to terminate the current.

For some applications, the contact region of each electrode on skin 22 is a circle having a diameter between about 10 and 100 microns. The inventors believe that this range is particularly suited for producing the very localized ablation desired by some embodiments of the present invention. It is noted that this size range is significantly different from other drug delivery techniques, such as electroporation, in which the contact area of electrodes on the skin may be, for example, 2 cm$^2$.

Preferably, ablation head 402 comprises an accelerometer or other mechanical disposition sensor 312, coupled to control unit 308, to enable the control unit to compute the velocity and distance traveled by device 400. If appropriate, velocity readings are displayed to the user on display 304 and/or output through speaker 306, for example, with one of the following messages: "Too slow," "Speed OK," or "Too fast." Alternatively or additionally, mechanical disposition sensor 312 comprises a force transducer, and control unit 308 is adapted to drive current through electrodes 320 only if the force between device 400 and skin 22 is above a minimum threshold.

For some applications, a pre-moistened medical patch of a known size is to be applied to the skin subsequent to ablation thereof by device 400. In such applications, control unit 308 preferably operates in a mode that prevents current flow to electrodes 320 after the device has ablated a user-specified distance on the skin. Additionally or alternatively, the distance traveled by device 400 is displayed to the user on display 304 such that he/she can pass device 400 over a desired distance, treating a specified length of skin, and then stop when the desired distance has been treated.

Ablation head 402 preferably comprises an ink reservoir 326, coupled to the surface of the ablation head by an ink conduit 328, such that areas of skin 22 in which micro-channels are formed are demarcated by a deposit of ink. In another preferred embodiment, a pre-moistened ink pad (not shown) is affixed to ablation head 402. In either case, following the use of handheld device 400 to prepare an area of skin 22 for subsequent administration of an active substance or extraction of an analyte, the treated area of skin 22 is clearly identifiable to the user. Alternatively or additionally, visible dimples are temporarily formed on skin 22 by protrusive elements on ablation head 402, as device 400 is passed over the skin. If appropriate, electrodes 320 may be shaped to form the protrusive elements. Alternatively, the protrusive elements are integrated into the outer surface of ablation head 402, or elsewhere on device 400. In a preferred embodiment, device 400 only applies current to skin 22 if the force applied by the device onto the skin is greater than a threshold expected to produce such visible dimples.

Figure 13:
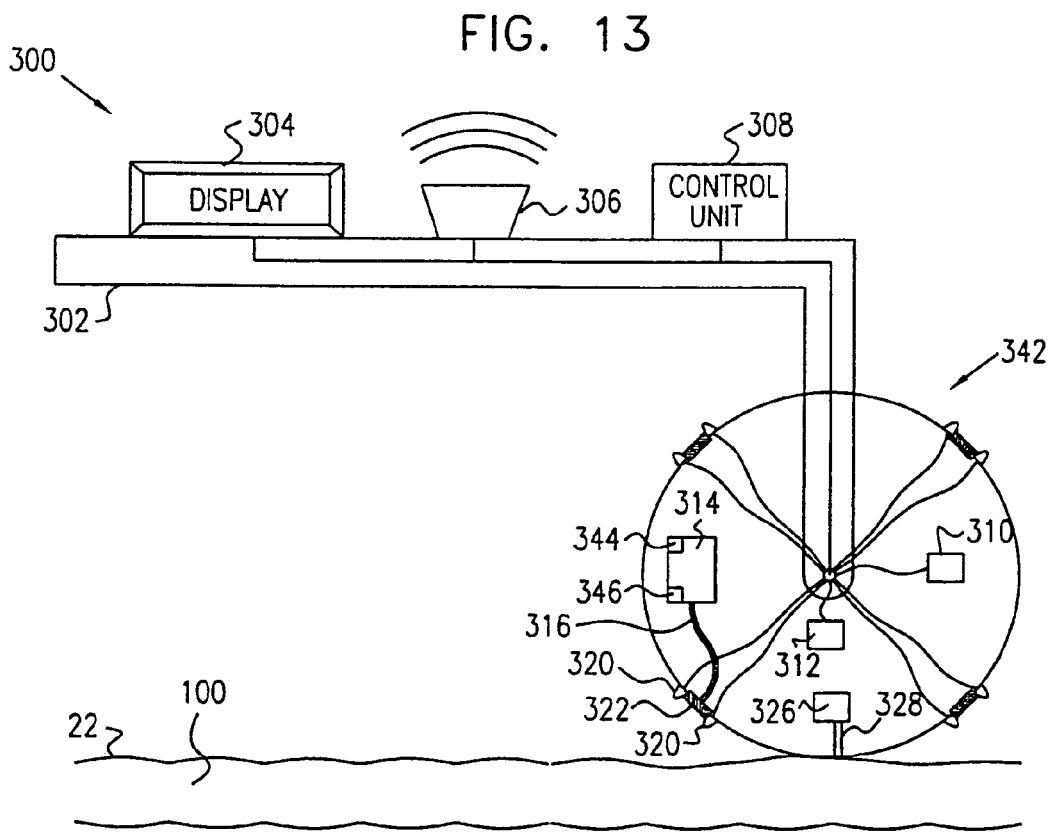
FIG. 13 is a schematic, partly sectional illustration of handheld apparatus for transdermal transport of a substance, in accordance with another preferred embodiment of the present invention.

FIG. 13 is a schematic, partly sectional illustration of a handheld device 300 for transdermal delivery of an active substance and/or transdermal analyte extraction, in accordance with a preferred embodiment of the present invention. Device 300 preferably comprises handle 302, to which is attached control unit 308, display 304, speaker 306, and an ablation head 342. Except for differences described hereinbelow, device 300 is typically constructed in a manner substantially similar to device 400. Ablation head 342 preferably rotates as it moves across skin 22, causing one or more pairs of adjacent electrodes 320 to repeatedly come into contact and out of contact with the skin. Preferably, electrodes 320 are driven by control unit 308 to form micro-channels in stratum corneum 100 as the ablation head moves along skin 22.

Preferably, although not necessarily, a porous material 322 is affixed between or in a vicinity of adjacent electrodes 320. Porous material 322 is typically used for delivery of an active substance to the surface of skin 22, in the region of the micro-channels formed by electrodes 320. Alternatively or additionally, porous material 322 is used to extract molecules from the underlying tissue, which pass through the newly-formed micro-channels, generally for diagnostic purposes. Porous material 322 is typically selected using criteria such as the size or other characteristics of the molecules of active substance or analyte, and the desired rate of transfer of the active substance or analyte.

In a preferred embodiment, ablation head 342 comprises a drug reservoir 314, which is preferably reusable, such that it can be refilled with an active substance for subsequent treatments. Alternatively, disposable cartridges containing a fixed amount of the active substance are inserted into ablation head 342 prior to use. Drug reservoir 314 preferably comprises a reservoir gauge 346 to determine the amount of active substance remaining in drug reservoir 314. In a preferred embodiment, the output of gauge 346 is passively displayed, e.g., through a window on the reservoir. Alternatively or additionally, a gauge output signal is passed to control unit 308, and logic in the control unit processes the signal so as to determine the amount of active substance remaining in drug reservoir 314 and/or the amount of active substance administered in the current application of device 300. This information is preferably presented to the user on display 304. Alternatively or additionally, an audio signal from speaker 306 informs the user when the drug reservoir is empty, indicates when a desired quantity of active substance has been delivered to skin 22, or conveys other relevant information regarding the status of device 300.

Preferably, drug reservoir 314 comprises a reservoir pump 344, which is driven by control unit 308 so as to regulate the flow rate of the active substance to porous material 322. Alternatively or additionally, the flow of active substance produced by reservoir pump 344 forms a spray of active substance at the exit of a drug conduit 316 leading from the reservoir. The spray, in turn, coats the ablated region of skin 22 with the active substance. Consequently, porous material 322 may be eliminated in this embodiment. Alternatively, a hole in porous material 322 allows the spray to pass therethrough, while the surrounding porous material absorbs any active substance not initially absorbed into skin 22, and keeps the substance in contact with the skin for later absorption.

It is to be understood that, whereas some preferred embodiments of the present invention are described herein with respect to administration of a drug in a liquid form through the skin, in other preferred embodiments of the present invention, the drug is administered in another form, e.g., as a powder or a gel pre-applied around the electrodes.

Ablation head 342 typically comprises a position sensor 310, coupled to measure the angular position of the ablation head and to send a signal responsive thereto to control unit 308. The control unit preferably determines the velocity and position of device 300, and outputs instructions to the user based on these determinations, as described hereinabove. Alternatively or additionally, the angular position of the ablation head is used by the control unit in regulating the timing of the application of electric current to electrodes 320. Further alternatively or additionally, porous material 322 is actively wetted with the active substance an appropriate amount of time or distance before the porous material comes in contact with the skin. This is particularly useful if the active substance has a high evaporation rate, and/or if the substance is applied to the skin as a spray.

Figure 14:
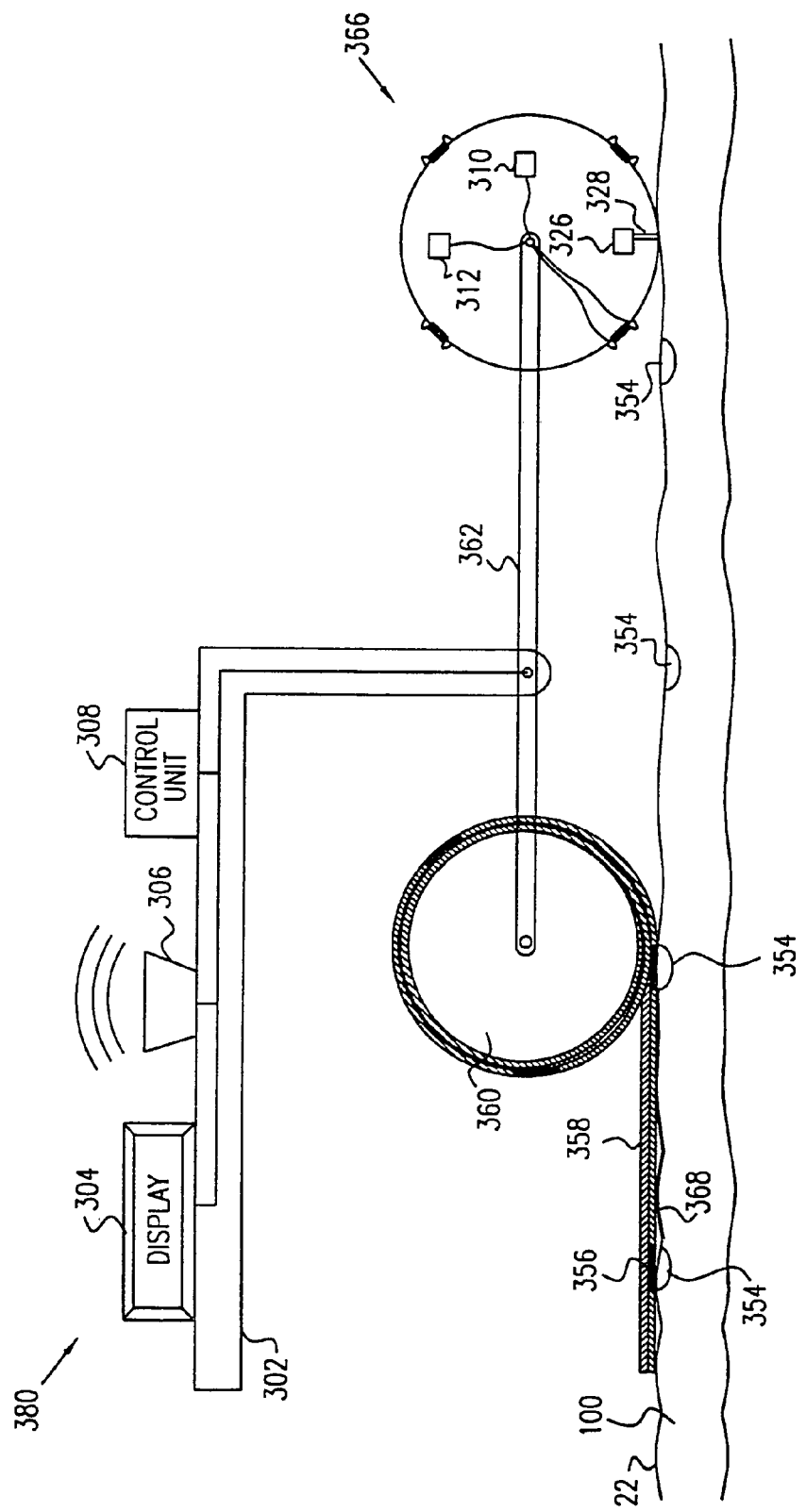
FIG. 14 is a schematic, partly sectional illustration of handheld apparatus for transdermal transport of a substance, in accordance with still another embodiment of the present invention.

FIG. 14 is a schematic, partly sectional illustration of a device 380 for transdermal delivery of an active substance or transdermal analyte extraction, in accordance with another preferred embodiment of the present invention. Device 380 preferably operates in substantially the same manner as device 300, described hereinabove with reference to FIG. 13, but device 380 utilizes different apparatus for delivering the active substance to the surface of skin 22. Whereas in device 300 the means for active substance delivery are integrated into ablation head 342, device 380 includes separate apparatus for delivering the active substance to skin 22.

Device 380 preferably comprises a rocker arm 362, coupled between ablation head 366 and a drug delivery spool 360. Preferably, ablation head 366 is free to rotate as device 380 is moved across the surface of the skin, causing electrodes 320 to repeatedly come into and out of contact with the skin such that micro-channels are formed in the stratum corneum, as described hereinabove. Drug delivery spool 360, according to this embodiment, is coupled to rocker arm 362 such that the spool is free to rotate as device 380 moves across skin 22. Preferably, the active substance is delivered to the ablated region of the skin by means of a drug delivery strip 358 to which the active substance has been pre-applied (e.g., at the time of manufacture). An adhesive coating 368 on strip 358 preferably holds the strip in place on the ablated region of the skin. In a preferred embodiment, strip 358 and spool 360 are combined as a single disposable unit, so that prior to use, the user attaches the pre-wound spool to rocker arm 362. Alternatively, drug delivery strip 358 is wound around drug delivery spool 360 by the user, such that spool 360 is reusable while strip 358 is disposable. Further alternatively, strip 358 is divided into a number of sections, corresponding to individual patches, each containing one dose of the drug, such that as the user passes device 380 over skin 22, one patch is placed onto the skin. Thereafter, the patch is preferably separated from the strip at a line of perforations (not shown).

In a preferred embodiment, the active substance is uniformly applied to drug delivery strip 358. Alternatively, the active substance is applied at discrete locations 356 on drug delivery strip 358. In this case, the delivery strip is preferably applied to the ablated region of skin 22 in a manner which aligns locations 356 with ablation sites 354 in skin 22 induced by ablation head 366.

It is noted that FIG. 14 illustrates device 380 in a configuration in which ablation head 366 precedes drug delivery spool 360 as device 380 is moved across the skin. It is to be understood, however, that alternative embodiments may include a drug delivery spool preceding ablation head 342 as the device moves over the skin. In such a case, electrodes 320 typically either puncture drug delivery strip 358 or protrude through pre-formed holes (not shown) in the delivery strip prior to ablating skin 22. Further alternatively, strip 358 is itself wound around ablation head 366, such that the act of rolling the ablation head over skin 22 both triggers electrodes protruding through holes in the strip to create the micro-channels, and also causes the strip to unwind from the ablation head and remain in contact with the skin. In these embodiments, the active substance is in contact with the skin as electrodes 320 form micro-channels in the skin, which may be preferable for certain applications.

Figure 15:
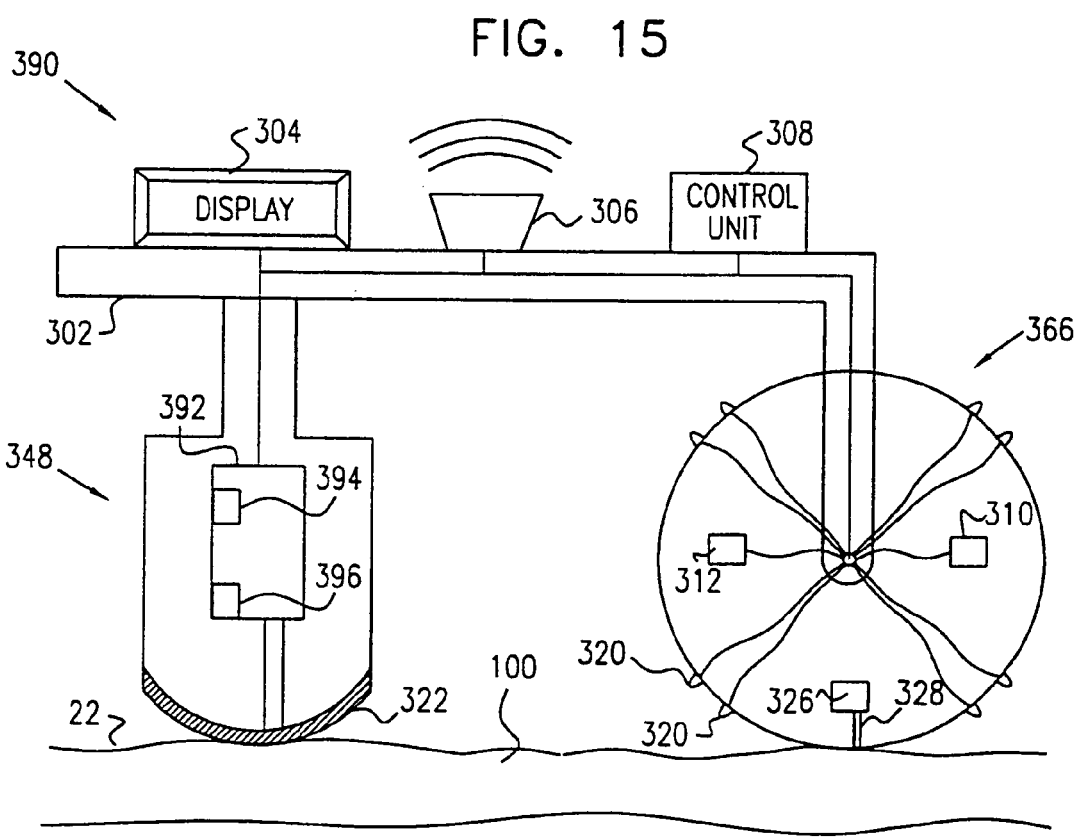
FIG. 15 is a schematic, partly sectional illustration of handheld apparatus for transdermal transport of a substance, in accordance with yet another preferred embodiment of the present invention.

FIG. 15 is a schematic, partly sectional illustration of a device 390 for transdermal delivery of an active substance or transdermal analyte extraction, in accordance with a preferred embodiment of the present invention. Device 390 preferably operates in substantially the same manner as device 380, described hereinabove with reference to FIG. 14, but device 390 has different means for delivering the active substance to the surface of skin 22. Preferably, device 390 comprises a drug delivery head 348, coupled to handle 302, for delivery of the active substance to the surface of the skin.

Preferably, drug delivery head 348 comprises a drug reservoir 392 containing the active substance, and a porous material 322 through which the active substance flows during operation of device 390. A desired flow rate of the active substance is typically achieved under the influence of gravity and/or capillary action in porous material 322. Alternatively or additionally, drug reservoir 392 comprises a reservoir pump 394 coupled to control unit 308, so as to allow the flow rate of the active substance to be actively controlled, as described hereinabove. In either case, porous material 322 typically slides along skin 22 as device 390 is moved over the skin. Alternatively, drug delivery head 348 is coupled to rotate as device 390 moves along the skin.

FIG. 16 is a schematic pictorial illustration of a device 500 for transdermal delivery of an active substance or transdermal analyte extraction, in accordance with a preferred embodiment of the present invention. Device 500 preferably operates in a generally similar manner to that described hereinabove with reference to FIGS. 12–15, except as noted below. Device 500 preferably comprises an ablation head 510 having a large number of small "monopolar" electrodes 512 disposed thereon. In addition, one or more larger return electrodes 514 are preferably disposed on ablation head 510, and serve as a return conduit for current driven through the skin by electrodes 512.

It is to be understood that any of the drug delivery or analyte extraction devices described hereinabove may similarly comprise a plurality of current-driving electrodes and one or more return electrodes. In general, monopolar devices tend to produce ablation of the stratum corneum directly under and immediately adjacent to the site of each current-driving electrode. Because of the typically larger size of the return electrodes, there is usually no substantial heating of the skin thereunder.

Figure 17A:
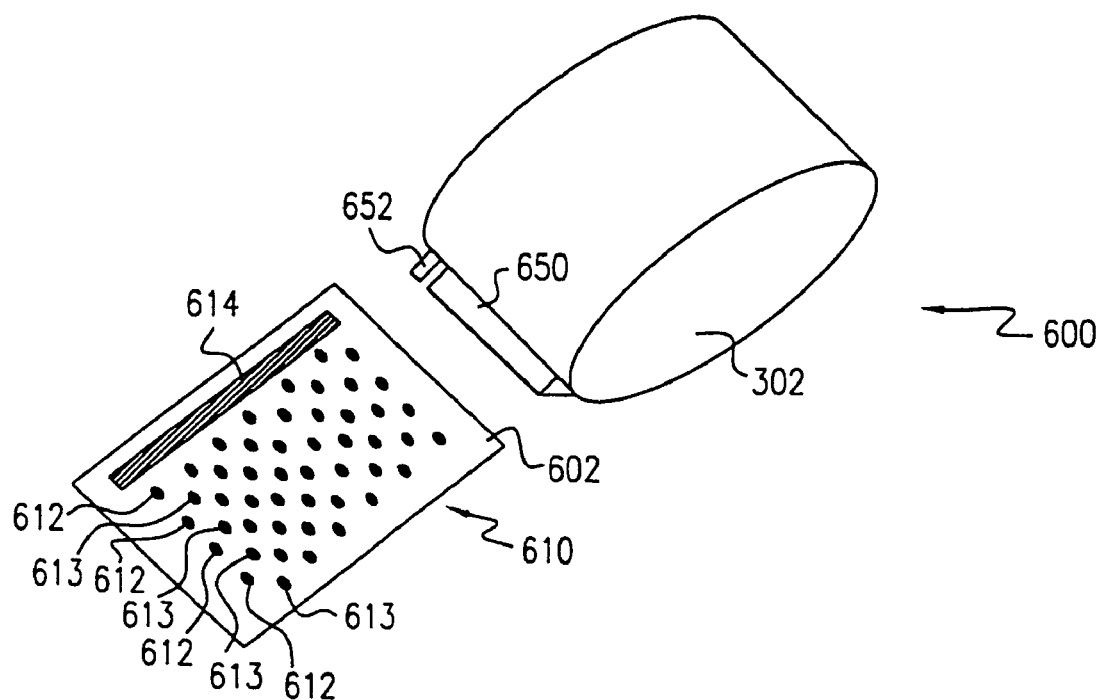
FIGS. 17A and 17B are schematic illustrations of handheld apparatus for enabling transdermal transport of a substance, in accordance with still an additional preferred embodiment of the present invention.
Figure 17B:
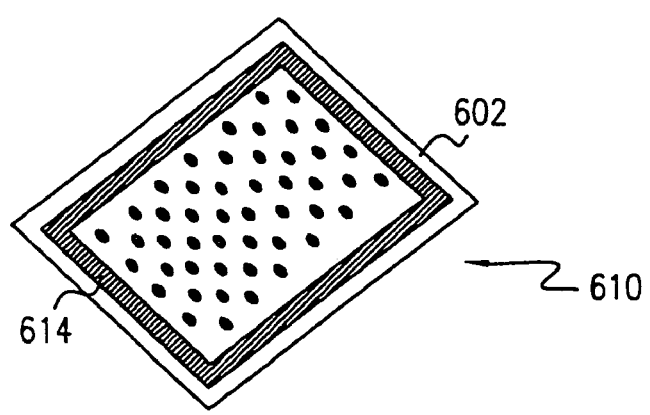

FIGS. 17A and 17B are schematic illustrations of apparatus 600 for enabling transdermal transport of a substance, in accordance with a preferred embodiment of the present invention. Except for differences described hereinbelow, apparatus 600 is preferably configured to operate generally in accordance with some or all of the techniques described herein for ablating stratum corneum.

Preferably, a handheld unit including at least one high-voltage driving electrode 650, a return electrode 652, and a power source (not shown) is passed by the user over a patch 602, which typically comprises a set of monopolar receiving electrodes 610 and a return strip 614. Electrodes 610 and return strip 614 preferably pass through patch 620 from the top surface thereof (FIG. 17A) to the bottom surface thereof (FIG. 17B), so as to contact skin 22 when the patch is placed on the skin. Alternatively, the electrodes are configured by other means to electrically connect the top and bottom surfaces of patch 620. In this manner, as the handheld unit is passed over the patch, driving electrode 650 preferably comes into contact with each of receiving electrodes 610, and drives current through these electrodes into skin 22. Simultaneously, return electrode 652 makes contact with return strip 614 on patch 602, allowing current injected into skin 22 to return to the handheld unit. Preferably, the current is configured so as to produce local ablation at the contact sites of each of electrodes 610 with skin 22. There is typically no substantial heating where return strip 614 contacts the skin, because the strip preferably has a significantly larger contact area than the total contact area of each of electrodes 610.

For some applications, the location of each of electrodes 610 on patch 602 is arranged such that as the handheld unit is passed over the patch, driving electrode 650 makes simultaneous contact with a desired number of electrodes 612 before contacting a subsequent group of one or more electrodes 613. Thus, as appropriate, electrodes 610 may be arranged in: (a) a staggered grid (FIGS. 17A and 17B), (b) a rectangular grid, with one or more electrodes in each dimension, or (c) a line parallel to return strip 614, so as to allow only one electrode to be contacted at a time. Alternatively or additionally, other geometries are used so as to provide contact, at any given time, between one or more of electrodes 610 and driving electrode 650.

Preferably, the shape of the surface of patch 602 is configured in accordance with the desired motion of the handheld unit. For example, return strip 614 may be recessed into the surface of the patch, in a manner which facilitates desired contact between the handheld unit and the patch.

If appropriate, the power source may be configured to apply the current such that two or more passes of the handheld unit over the patch produce the desired extent of ablation of the stratum corneum. It is noted that although the handheld unit is shown in FIGS. 17A and 17B as being configured for manual operation, automated means may also be provided for moving driving electrode 650 over each of electrodes 610 on patch 602.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A device for ablating stratum corneum epidermidis of skin on the body of a subject, comprising:
   a plurality of electrodes, which are adapted to be applied to the skin of the subject at respective points; and
   a power source, which is adapted to apply electrical energy between two or more of the plurality of electrodes, to cause ablation of an area of the stratum corneum during a first time period, so as to facilitate passage of a substance through the ablated area into the body during a second time period, subsequent to the first time period,
   wherein the power source is adapted to apply the electrical energy as alternating current,
   wherein the plurality of electrodes comprise a common electrode and a plurality of positive electrodes, and
   wherein the power source is configured such that, during a phase of the alternating current, the alternating current from the power source flows from each positive electrode, through the skin, to the common electrode.

2. A device for ablating stratum corneum epidermidis of skin on the body of a subject, comprising:
   a plurality of electrodes, which are adapted to be applied to the skin of the subject at respective points;
   a power source, which is adapted to apply electrical energy between two or more of the plurality of electrodes, to cause ablation of an area of the stratum corneum during a first time period, so as to facilitate passage of a substance through the ablated area during a second time period, subsequent to the first time period; and
   a plurality of resistors, coupled to the plurality of electrodes.

3. The device according to claim 2, wherein each resistor is coupled to a respective one of the plurality of electrodes.

4. The device according to claim 2, wherein the power source is adapted to drive the current from a first one of the electrodes, through the stratum corneum, to a plurality of other ones of the electrodes.

5. The device according to claim 2, wherein the power source is adapted to apply the electrical energy as alternating current.

6. A device for ablating stratum corneum epidermidis of skin on the body of a subject, comprising:
   a plurality of electrodes, which are adapted to be applied to the skin of the subject at respective points; and
   a power source, which is adapted to apply electrical energy between two or more of the plurality of electrodes, to cause ablation of an area of the stratum corneum during a first time period, so as to facilitate passage of a substance through the ablated area into the body during a second time period, subsequent to the first time period,
   wherein the two or more of the plurality of electrodes comprise: (a) a plurality of current-driving electrodes, and (b) a plurality of return electrodes, and
   wherein, in applying the electrical energy, the power source is adapted to drive current from the current-driving electrodes, through the stratum corneum, to the plurality of return electrodes.

* * * * *